(12) United States Patent
Marat

(10) Patent No.: US 8,937,187 B2
(45) Date of Patent: Jan. 20, 2015

(54) METHOD FOR DEPIGMENTING KERATIN MATERIALS USING RESORCINOL DERIVATIVES

(75) Inventor: Xavier Marat, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/994,917

(22) PCT Filed: Nov. 23, 2011

(86) PCT No.: PCT/EP2011/070816
§ 371 (c)(1),
(2), (4) Date: Jul. 10, 2013

(87) PCT Pub. No.: WO2012/079938
PCT Pub. Date: Jun. 21, 2012

(65) Prior Publication Data
US 2013/0281507 A1  Oct. 24, 2013

Related U.S. Application Data

(60) Provisional application No. 61/425,260, filed on Dec. 21, 2010.

(30) Foreign Application Priority Data

Dec. 16, 2010  (FR) ...................... 10 60635

(51) Int. Cl.
C07D 207/12 (2006.01)
C07D 311/20 (2006.01)
A61K 31/4015 (2006.01)
A61Q 19/02 (2006.01)
A61K 8/49 (2006.01)
C07D 207/404 (2006.01)
C07D 207/46 (2006.01)
C07D 403/08 (2006.01)

(52) U.S. Cl.
CPC ............ *A61K 8/4913* (2013.01); *C07D 207/12* (2013.01); *A61K 31/4015* (2013.01); *C07D 207/404* (2013.01); *C07D 207/46* (2013.01); *C07D 311/20* (2013.01); *C07D 403/08* (2013.01); *A61Q 19/02* (2013.01)
USPC ............................ 548/547; 549/399; 514/425

(58) Field of Classification Search
CPC ............... C07D 207/12; C07D 311/20; A61K 31/4015; A61Q 19/02
USPC ............................ 548/547; 549/399; 514/425
See application file for complete search history.

(56) References Cited

U.S. PATENT DOCUMENTS 5,536,500 A  7/1996 Galey et al.

FOREIGN PATENT DOCUMENTS

EP  0 664 290  7/1995
EP  1 774 958  4/2007

OTHER PUBLICATIONS

International Search Report Issued Jan. 27, 2012 in PCT/EP11/70816 Filed Nov. 23, 2011.

*Primary Examiner* — Robert Havlin
(74) *Attorney, Agent, or Firm* — Oblon, Spivak, McClelland, Maier & Neustadt, L.L.P.

(57) ABSTRACT

The invention relates to compounds of formula (I): The invention likewise relates to a cosmetic method for depigmenting, lightening and/or whitening keratin materials, more particularly the skin, that utilizes these compounds.

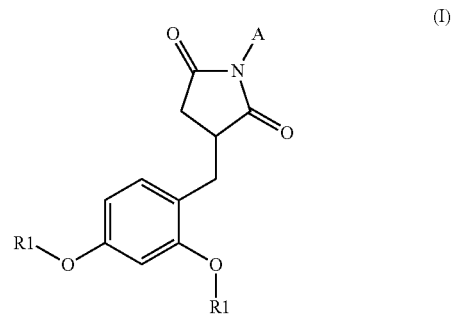

17 Claims, No Drawings

METHOD FOR DEPIGMENTING KERATIN MATERIALS USING RESORCINOL DERIVATIVES

The present invention relates to new compounds which are resorcinol derivatives and to a method for cosmetic treatment, particularly for depigmenting and/or whitening the skin, that employs such a compound.

At different periods in their life, certain people develop darker and/or more coloured marks on their skin, and more particularly on the hands and face, which give the skin a heterogeneous appearance. These marks are due in particular to a high concentration of melanin in the keratinocytes located at the surface of the skin.

The use of harmless topical depigmenting substances which exhibit good efficacy is especially desirable in order to treat pigmentary marks.

The mechanism of formation of the skin's pigmentation, in other words the formation of melanin, is particularly complex, and involves, schematically, the following principal steps:

Tyrosine--->Dopa--->Dopaquinone--->Dopachrome--->Melanin

Tyrosinase (monophenol dihydroxyl phenylalanine: oxygen oxidoreductase EC 1.14.18.1) is the essential enzyme participating in this sequence of reactions. In particular it catalyses the reaction converting tyrosine into dopa (dihydroxyphenylalanine), by virtue of its hydroxylase activity, and the reaction converting dopa into dopaquinone, by virtue of its oxidase activity. This tyrosinase acts only when it is in the mature form, under the action of certain biological factors.

A substance is acknowledged as being depigmenting if it acts directly on the vitality of the epidermal melanocytes, where melanogenesis takes place, and/or if it interferes with one of the steps in the biosynthesis of melanin, either by inhibiting one of the enzymes involved in melanogenesis, or by inserting itself as a structural analogue of one of the chemical compounds of the melanin synthesis chain; this chain may then become blocked and may thus ensure depigmentation.

Arbutin and kojic acid are known as depigmenting agents for the skin.

Substances have been sought which exhibit an effective depigmenting action which in particular is greater than that of arbutin and of kojic acid.

In this regard, the Applicant has found, surprisingly and unexpectedly, that certain compounds derived from resorcinol exhibit good depigmenting activity even at low concentration.

The invention accordingly provides new compounds of formula (I) as defined below.

The invention also provides a composition comprising, in a physiologically acceptable medium, at least one compound of formula (I) as defined below.

The invention likewise provides a non-therapeutic, cosmetic method for depigmentation, lightening and/or whitening of keratin materials, more particularly the skin, which comprises applying the composition described above.

The invention also provides for the non-therapeutic, cosmetic use of a compound of formula (I) as a whitening, lightening and/or depigmenting agent for keratin materials, more particularly the skin.

The compounds according to the invention allow effective depigmenting and/or lightening, or even whitening, of the skin of human beings. They are intended more particularly for application to the skin of individuals presenting brownish pigmentation marks or senescence marks, or to the skin of individuals who wish to combat the appearance of a brownish colour arising from melanogenesis.

They may also allow depigmentation and/or lightening of the body hair, eyelashes, head hair and also the lips and/or the nails.

The new compounds according to the invention therefore conform to formula (I) below:

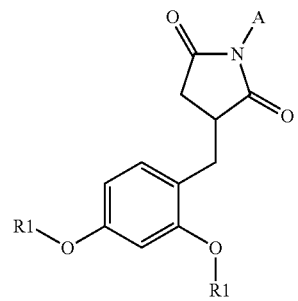

in which:

R$_1$ denotes a hydrogen atom or an acetyl group;

A denotes a radical selected from:

a) —H;

b) -a C$_3$-C$_8$ cyclic or C$_3$-C$_{20}$ branched or C$_2$-C$_{20}$ unsaturated or C$_1$-C$_{20}$ saturated linear alkyl group which is optionally interrupted by one or more heteroatoms or moieties selected from N, O and —CO— or a combination thereof such as —NHCO—, —NHCONH— and/or is optionally substituted by one or more identical or different groups selected from:

i) —OR$_5$
ii) —SR$_5$
iii) —NR$_6$R$_7$
iv) —CONHR$_6$
v) —CONR$_6$R$_7$
vi) —COOR$_6$
vii) —NHCONHR$_6$
viii) —C(O)C$_1$-C$_4$alkyl
ix) a C$_5$-C$_{12}$ (hetero)aryl group optionally containing one or more heteroatoms selected from O, N and S and optionally substituted by one or more hydroxyls and/or by one or more C$_1$-C$_8$ alkoxy radicals;
x) a saturated or unsaturated, non-aromatic heterocycle having from 5 to 8 members and comprising one or more heteroatoms selected from O, N and S which is optionally substituted by one or more hydroxyls and/or by one or more C$_1$-C$_8$ alkoxy or C$_1$-C$_4$ alkyl radicals, it being possible for one of the members to be a carbonyl group;

c) -a C$_5$-C$_{12}$ (hetero)aryl group optionally containing one or more heteroatoms selected from O, N and S and optionally substituted by one or more hydroxyls and/or by one or more radicals selected from C$_1$-C$_8$ alkoxy or C$_1$-C$_8$ alkyl groups;

d) —NR$_2$R$_3$;
e) —OR$_4$;
f) —C(O)NHR$_4$;
g) C(O)C$_1$-C$_{10}$alkyl where R$_2$ and R$_3$, which are identical or different, denote a radical selected from:

a) —H;
b) -a C$_3$-C$_8$ cyclic or C$_3$-C$_{10}$ branched or C$_2$-C$_{10}$ unsaturated or C$_1$-C$_{10}$ linear saturated alkyl group which is optionally interrupted by one or more heteroatoms or moieties selected from N, O and —CO— or a combination thereof such as —NHCO—, —NHCONH— and/or is optionally substituted by one or more identical or different groups selected from —OR$_5$;

c) a $C_5$-$C_{12}$ (hetero)aryl group optionally containing one or more heteroatoms selected from O, N and S and optionally substituted by one or more hydroxyls and/or by one or more $C_1$-$C_8$ alkoxy radicals; it being possible for $R_2$ and $R_3$ to form, with the nitrogen which carries them, a heterocycle which has from 5 to 8 members and may contain one or more heteroatoms or moieties selected from N, O and —CO— and/or is optionally substituted by a $C_1$-$C_{10}$ hydrocarbon chain optionally containing one or more radicals selected from hydroxyl or $C_1$-$C_4$ alkoxy;

$R_4$ denotes a radical selected from:

a) —H b) a $C_3$-$C_8$ cyclic or $C_3$-$C_{10}$ branched or $C_1$-$C_{10}$ linear saturated alkyl group which is optionally substituted by one or more identical or different groups selected from:

i) —COOR$_6$, ii) a $C_5$-$C_{12}$ (hetero)aryl radical which optionally contains one or more heteroatoms selected from O, N and S and is optionally substituted by one or more hydroxyls and/or by one or more $C_1$-$C_8$ alkoxy radicals;

c) a $C_5$-$C_{12}$ (hetero)aryl group which optionally contains one or more heteroatoms selected from O, N and S and is optionally substituted by one or more hydroxyls and/or by one or more $C_1$-$C_8$ alkoxy radicals;

$R_5$ is selected from H and a $C_3$-$C_8$ cyclic or $C_2$-$C_{10}$ unsaturated or $C_3$-$C_{10}$ branched or $C_1$-$C_{10}$ linear saturated alkyl hydrocarbon group;

$R_6$ and $R_7$, which are identical or different, are selected from H, a $C_3$-$C_8$ cyclic or $C_2$-$C_{10}$ unsaturated or $C_3$-$C_{10}$ branched or $C_1$-$C_{10}$ linear saturated alkyl hydrocarbon group; a ($C_1$-$C_4$)alkyl-$C_6$ (hetero)aryl group optionally containing a nitrogen atom, more particularly a benzyl group;

$R_6$ and $R_7$ may form, with the nitrogen which carries them, a heterocycle which has from 5 to 8 members and may contain one or more heteroatoms or moieties selected from N, O and —CO— and/or is optionally substituted by a $C_1$-$C_{10}$ hydrocarbon chain;

h) a radical of formula (II):

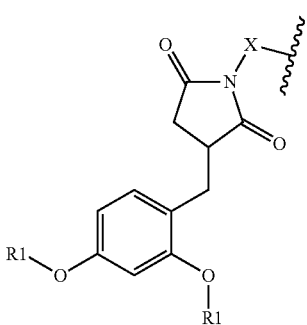

(II)

in which:

X denotes $C_3$-$C_8$ cyclic or $C_3$-$C_{10}$ branched or $C_1$-$C_{10}$ linear saturated hydrocarbon chain or a $C_6$-$C_{12}$ arylene group such as phenylene, or a $C_1$-$C_4$ alkylene-$C_6$-$C_8$ cycloalkylene-$C_1$-$C_4$ alkylene group or a $C_1$-$C_4$ alkylene-phenylene-$C_1$-$C_4$ alkylene group, which is optionally substituted by one or more identical or different radicals selected from —OH, —COOR$_6$ where $R_6$ denotes H or a $C_3$-$C_8$ cyclic or $C_2$-$C_{10}$ unsaturated or $C_3$-$C_{10}$ branched or $C_1$-$C_{20}$ linear saturated alkyl hydrocarbon group;

$R_1$ denotes a hydrogen atom or an acetyl group;

and, when A denotes a radical of formula (II), all of the radicals $R_1$ in the compounds of formula (I) are identical;

and also their salts, their solvates, their optical isomers and their racemates.

The salts of the compounds of formula (I) include conventional non-toxic salts of said compounds, such as those formed from acid or from base.

Salts of the compound of formula (I) (when it comprises a quaternizable nitrogen atom), include the following:

a) salts obtained by addition of the compound (I) with a mineral acid, selected more particularly from hydrochloric, boric, hydrobromic, hydroic, sulphuric, nitric, carbonic, phosphoric and tetrafluoroboric acids;

b) or the salts obtained by addition of the compound (I) with an organic acid, more particularly selected from acetic, propionic, succinic, fumaric, lactic, glycolic, citric, gluconic, salicylic, tartaric, terephthalic, methylsulphonic, ethylsulphonic, benzene sulphonic, toluene sulphonic and triflic acids.

Also included are the salts obtained by addition of the compound of formula (I) (when it comprises an acidic group) with a mineral base, such as aqueous sodium hydroxide and potassium hydroxide, calcium hydroxide, ammonium hydroxide, magnesium hydroxide, lithium hydroxide, and sodium, potassium or calcium carbonates or hydrogencarbonates, for example;

or with an organic base such as a primary, secondary or tertiary alkylamine, for example triethylamine or butylamine. This primary, secondary or tertiary alkylamine may comprise one or more nitrogen and/or oxygen atoms and may therefore comprise, for example, one or more alcohol functions; included more particularly are 2-amino-2-methylpropanol, ethanolamine, triethanolamine, 2-dimethylamino propanol, 2-amino-2-(hydroxymethyl)-1,3-propanediol and 3-(dimethylamino)propylamine.

Also included are the salts of amino acids such as, for example, lysine, arginine, guanidine, glutamic acid and aspartic acid.

The salts of the compounds of formula (I) (when it comprises an acidic group) may advantageously be selected from alkali metal salts or alkaline earth metal salts such as sodium, potassium, calcium and magnesium salts; and ammonium salts.

The salts of the compounds of formula (I) (when it comprises a quaternizable nitrogen atom) may advantageously be selected from halides such as chloride and bromide; and from citrates, acetates, succinates, phosphates, lactates and tartrates.

The acceptable solvates of the compounds described in the present invention comprise conventional solvates such as those formed during the preparation of said compounds as a result of the presence of solvents. Examples include the solvates resulting from the presence of water or of linear or branched alcohols such as ethanol or isopropanol.

The optical isomers are more particularly enantiomers and diastereoisomers.

The linear or branched groups may preferably be selected from methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl.

The saturated linear or branched alkyl groups may more preferably be selected from methyl, ethyl, propyl, isopropyl, butyl, isobutyl, tert-butyl, pentyl, hexyl, heptyl and octyl.

The $C_1$-$C_4$ alkoxy groups may preferably be selected from methoxy, ethoxy, propoxy and butoxy and more preferably methoxy.

The compounds of formula (I) preferably have the following meanings:

$R_1$ denotes a hydrogen atom or an acetyl group;

A denotes a radical selected from:

a) —H b) a $C_3$-$C_8$ cyclic or $C_3$-$C_{16}$ branched or $C_2$-$C_{16}$ unsaturated or $C_1$-$C_{16}$ linear saturated alkyl group which is optionally interrupted by one or more heteroatoms or moieties selected from N, O, —CO— and —NHC(O)— and/or is optionally substituted by one or more identical or different groups selected from:

i) —OH, ii) $C_1$-$C_4$ alkoxy, iii) —COOR$_6$, iv) —CONR$_6$R$_7$ where R$_6$ and R$_7$, which are identical or different, denote H or a $C_3$-$C_8$ cyclic or $C_2$-$C_8$ unsaturated or $C_3$-$C_8$ branched or $C_1$-$C_8$ linear saturated alkyl group;

v) a phenyl group which is optionally substituted by one or more hydroxyls and/or by one or more $C_1$-$C_4$ alkoxy radicals;

vi) a non-aromatic saturated or unsaturated heterocycle having from 5 to 8 members, comprising one or more heteroatoms selected from O, N and S, it being possible for one of the members to be a carbonyl group;

c) a $C_5$-$C_{12}$ aryl group such as phenyl which is optionally substituted by one or more identical or different radicals selected from OH, $C_1$-$C_4$ alkoxy and $C_1$-$C_4$ alkyl;

d) —NR$_2$R$_3$, where R$_2$ and R$_3$, which are identical or different, denote:

i) H;

ii) a $C_3$-$C_8$ cyclic or $C_2$-$C_8$ unsaturated or $C_3$-$C_8$ branched or $C_1$-$C_8$ linear saturated alkyl group which is optionally interrupted by an oxygen atom and/or is optionally substituted by a hydroxyl group or a $C_1$-$C_4$ alkoxy group such as methoxy;

iii) a $C_5$-$C_{12}$ aryl group which is optionally substituted by one or more hydroxyls and/or by one or more $C_1$-$C_4$ alkoxy radicals;

it being possible for R$_2$ and R$_3$ to form, with the nitrogen which carries them, a heterocycle having from 5 to 8 members, said heterocycle being able to contain one or more oxygen atoms and/or being optionally substituted by a $C_1$-$C_6$ hydrocarbon chain optionally containing one or more radicals selected from hydroxyl or $C_1$-$C_4$ alkoxy;

e) —OR$_4$ f) —C(O)NHR$_4$, where R$_4$ denotes a radical selected from —H, a $C_3$-$C_8$ branched or $C_1$-$C_8$ linear saturated alkyl group which is optionally substituted by one or more identical or different groups selected from:

i) —COOR$_6$, where R$_6$ is as defined above;

ii) a $C_5$-$C_{12}$ aryl radical, g) a radical of formula (II)

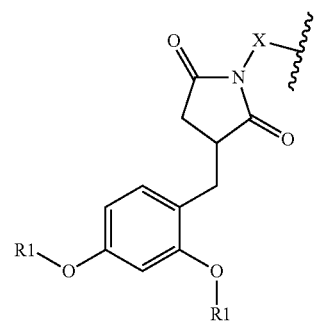

(II)

in which X denotes a $C_3$-$C_8$ cyclic or $C_3$-$C_6$ branched or $C_1$-$C_6$ linear saturated hydrocarbon chain or a $C_6$-$C_{12}$ arylene group such as phenylene, which is optionally substituted by one or more identical or different radicals selected from OH or a $C_1$-$C_6$ alkyl group, R$_1$ denotes a hydrogen atom or an acetyl group;

and also their salts, their solvates, their optical isomers and their racemates.

The compounds of formula (I) preferentially have the following meanings:

R$_1$ denotes a hydrogen atom or an acetyl group;

A denotes a radical selected from:

a) H b) a $C_3$-$C_8$ cyclic or $C_3$-$C_{16}$ branched or $C_2$-$C_{16}$ unsaturated or $C_1$-$C_{16}$ linear saturated alkyl group which is optionally interrupted by one or more heteroatoms selected from N and O and/or is optionally substituted by one or more identical or different groups selected from:

i) —OH ii) $C_1$-$C_4$ alkoxy, iii) —CONH$_2$;

iv) —COOR$_6$, where R$_6$ denotes H or a $C_3$-$C_4$ cyclic or $C_2$-$C_4$ unsaturated or $C_3$-$C_4$ branched or $C_1$-$C_4$ linear saturated alkyl group;

v) a phenyl group which is optionally substituted by one or more hydroxyls and/or by one or more $C_1$-$C_4$ alkoxy radicals;

vi) a saturated or unsaturated, non-aromatic heterocycle having from 5 to 8 members, comprising one or more nitrogen atoms, it being possible for one of the members to be a carbonyl moiety;

c) a $C_5$-$C_{12}$ aryl group such as phenyl;

d) —NR$_2$R$_3$, where R$_2$ and R$_3$, which are identical or different, denote H or a $C_3$-$C_8$ cyclic or $C_2$-$C_6$ unsaturated or $C_3$-$C_6$ branched or $C_1$-$C_6$ linear saturated alkyl group; or a $C_5$-$C_{12}$ aryl group such as phenyl;

it being possible for R$_2$ and R$_3$ to form, with the nitrogen which carries them, a heterocycle having from 5 to 8 members, it being possible for said heterocycle to contain an oxygen atom and/or being optionally substituted by a $C_1$-$C_6$ hydrocarbon chain optionally containing one or more radicals selected from hydroxyl or $C_1$-$C_4$ alkoxy;

e) —OR$_4$, where R$_4$ denotes H or a $C_3$-$C_6$ branched or $C_1$-$C_6$ linear saturated alkyl group which is optionally substituted by one or more identical or different groups selected from:

i) —COOH, ii) a $C_5$-$C_{12}$ aryl radical such as phenyl;

f) a radical of formula (II)

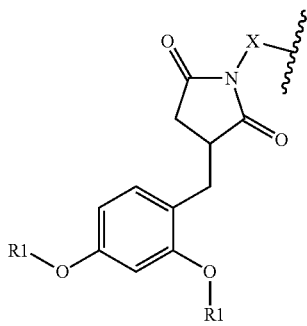

(II)

in which X denotes a $C_3$-$C_8$ cyclic or $C_3$-$C_6$ branched or $C_1$-$C_6$ linear saturated hydrocarbon chain or a $C_6$-$C_{12}$ arylene group such as phenylene, which is optionally substituted by one or more hydroxyl radicals;

and also their salts, their solvates, their optical isomers and their racemates.

Preferentially, $R_1$=H for the compounds of formula (I).

A number of embodiments of compounds of formula (I) are described below:

$R_1$=H and A=H (compound 1).

$R_1$=H and A=$C_3$-$C_{16}$ branched or $C_1$-$C_{16}$ saturated linear alkyl group (such as compounds 2-9).

$R_1$=H and A=$C_3$-$C_8$ branched or $C_1$-$C_8$ saturated linear alkyl group which is substituted by one or two hydroxyl groups and is optionally substituted by a group —$SR_5$, where $R_5$=H or $C_1$-$C_4$ alkyl (such as compounds 12-19).

$R_1$=H and A=phenyl or benzyl group (such as compounds 10 and 11).

$R_1$=H and A=$C_3$-$C_8$ branched or $C_1$-$C_8$ alkyl group which is substituted by a phenyl group which is optionally substituted by one or more hydroxyl groups and/or $C_1$-$C_4$ alkoxy group (such as compounds 20-22).

$R_1$=H and A=$C_3$-$C_8$ branched or $C_1$-$C_8$ saturated linear alkyl group which is substituted by a —COOH group, which is optionally substituted by a group $SR_5$, where $R_5$=H or $C_1$-$C_4$ alkyl (such as compounds 23-31).

$R_1$=H and A=$C_3$-$C_8$ branched or $C_1$-$C_8$ saturated linear alkyl group which is substituted by a group —$COOR_6$, where $R_6$ denotes a $C_1$-$C_6$ alkyl group, and is optionally substituted by a hydroxyl group and/or a group —$SR_5$, where $R_5$=H or $C_1$-$C_4$ alkyl and/or phenyl which is optionally substituted by one or more hydroxyls, or an imidazole radical (such as compounds 32-45).

$R_1$=H and A=$C_3$-$C_8$ branched or $C_1$-$C_8$ saturated linear alkyl group which is substituted by a —$CONH_2$ group, which is optionally substituted by a hydroxyl or phenyl group which is optionally substituted by one or more hydroxyls, or a group —$COOR_6$, where $R_6$ denotes a $C_1$-$C_6$ alkyl group (such as compounds 46-51).

$R_1$=H and A=group —$OR_4$, where $R_4$ denotes H, a $C_3$-$C_6$ branched or $C_1$-$C_6$ linear saturated alkyl group which is optionally substituted by a —COOH group or a phenyl group (such as compounds 55-59).

$R_1$=H and A=—$NR_2R_3$, where $R_2$ and $R_3$, which are identical or different, denote H or a $C_3$-$C_6$ branched or $C_1$-$C_6$ linear saturated alkyl group or a phenyl group;

it being possible for $R_2$ and $R_3$ to form, with the nitrogen which carries them, a heterocycle which has 5 or 6 members and may contain an oxygen atom, said heterocycle being optionally substituted by a $C_1$-$C_6$ hydrocarbon chain optionally containing one or more radicals selected from hydroxyl or $C_1$-$C_4$ alkoxy (such as compounds 60-64).

$R_1$=H and A=$C_3$-$C_6$ branched or $C_2$-$C_6$ linear alkyl group interrupted by a —CONH— group and substituted by a COOH group (such as compound 52).

$R_1$=H and A=$C_3$-$C_6$ cyclic alkyl group interrupted by a —CONH— group (such as compound 53).

$R_1$=H and A=$C_5$-$C_6$ cyclic alkyl group interrupted by an oxygen atom (such as compound 54).

$R_1$=H and A=radical of formula (II) as described above in which X denotes a $C_5$-$C_8$ cyclic or $C_3$-$C_6$ branched or $C_1$-$C_6$ linear saturated hydrocarbon chain or a phenylene group, which is optionally substituted by one or more hydroxyl groups (such as compounds 65-73).

Among the compounds of formula (I) it is preferred to use the following compounds:

| No. | Structure | Chemical name |
|---|---|---|
| 1 | 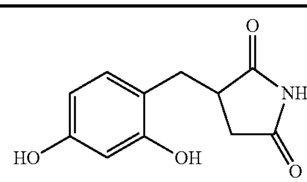 | 3-(2,4-dihydroxybenzyl)pyrrolidine-2,5-dione |
| 2 | 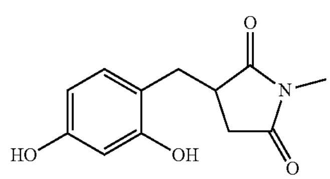 [SMILES: CN1C(=O)CC(Cc2ccc(O)cc2O)C1=O] | 3-(2,4-dihydroxybenzyl)-1-methylpyrrolidine-2,5-dione |
| 3 | 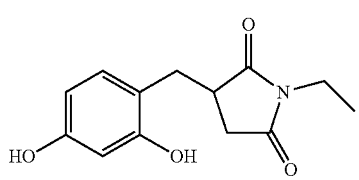 [SMILES: CCN1C(=O)CC(Cc2ccc(O)cc2O)C1=O] | 3-(2,4-dihydroxybenzyl)-1-ethylpyrrolidine-2,5-dione |

-continued
| No. | Structure | Chemical name |
|---|---|---|
| 4 | 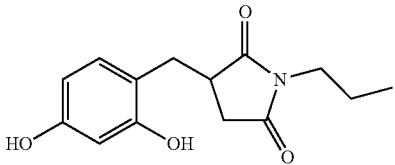 | 3-(2,4-dihydroxybenzyl)-1-propylpyrrolidine-2,5-dione |
| 5 | 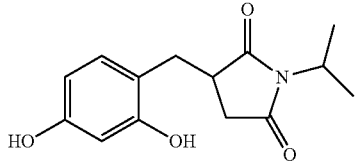 [SMILES: CC(C)N1C(=O)CC(Cc2ccc(O)cc2O)C1=O] | 3-(2,4-dihydroxybenzyl)-1-isopropylpyrrolidine-2,5-dione |
| 6 | 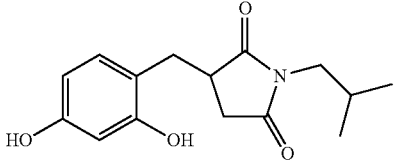 | 3-(2,4-dihydroxybenzyl)-1-isobutylpyrrolidine-2,5-dione |
| 7 | 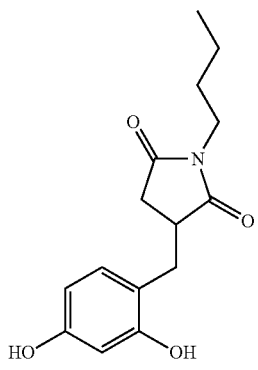 [SMILES: CCCCN1C(=O)CC(Cc2ccc(O)cc2O)C1=O] | 3-(2,4-dihydroxybenzyl)-1-butylpyrrolidine-2,5-dione |
| 8 | 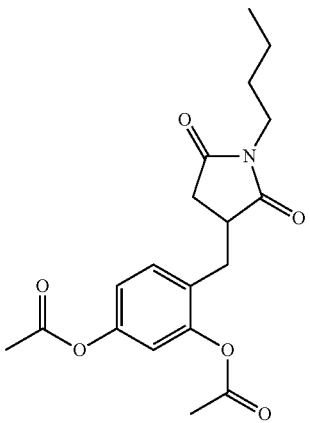 [SMILES: CCCCN1C(=O)CC(Cc2ccc(OC(C)=O)cc2OC(C)=O)C1=O] | 4-[(1-butyl-2,5-dioxopyrrolidin-3-yl)methyl]benzene-1,3-diyl diacetate |
| 9 | 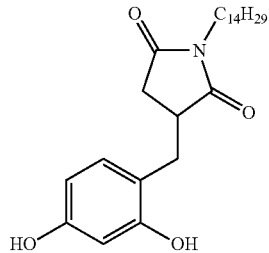 | 3-(2,4-dihydroxybenzyl)-1-tetradecylpyrrolidine-2,5-dione |

-continued

| No. | Structure | Chemical name |
|---|---|---|
| 10 | 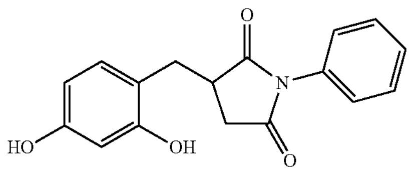 [SMILES: O=C1CC(Cc2ccc(O)cc2O)C(=O)N1c1ccccc1] | 3-(2,4-dihydroxybenzyl)-1-phenylpyrrolidine-2,5-dione |
| 11 | 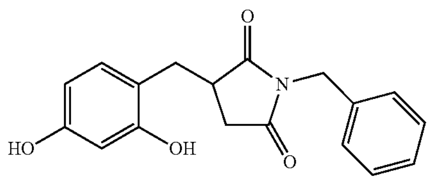 [SMILES: O=C1CC(Cc2ccc(O)cc2O)C(=O)N1Cc1ccccc1] | 3-(2,4-dihydroxybenzyl)-1-benzylpyrrolidine-2,5-dione |
| 12 | 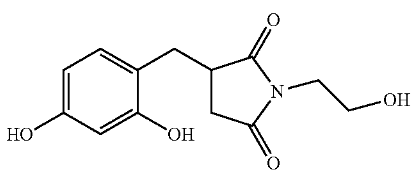 [SMILES: O=C1CC(Cc2ccc(O)cc2O)C(=O)N1CCO] | 3-(2,4-dihydroxybenzyl)-1-(2-hydroxyethyl)pyrrolidine-2,5-dione |
| 13 | 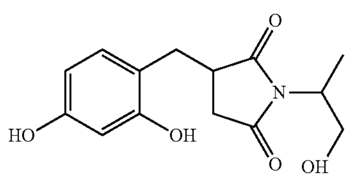 [SMILES: CC(CO)N1C(=O)CC(Cc2ccc(O)cc2O)C1=O] | 3-(2,4-dihydroxybenzyl)-1-(1-hydroxypropan-2-yl)pyrrolidine-2,5-dione |
| 14 | 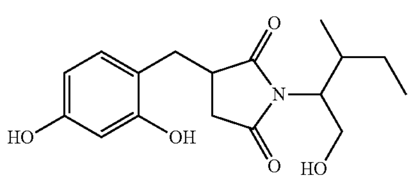 [SMILES: CCC(C)C(CO)N1C(=O)CC(Cc2ccc(O)cc2O)C1=O] | 3-(2,4-dihydroxybenzyl)-1-(1-hydroxy-3-methylpentan-2-yl)pyrrolidine-2,5-dione |
| 15 | 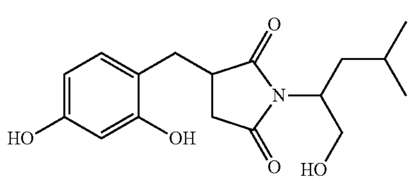 [SMILES: CC(C)CC(CO)N1C(=O)CC(Cc2ccc(O)cc2O)C1=O] | 3-(2,4-dihydroxybenzyl)-1-(1-hydroxy-4-methylpentan-2-yl)pyrrolidine-2,5-dione |
| 16 | 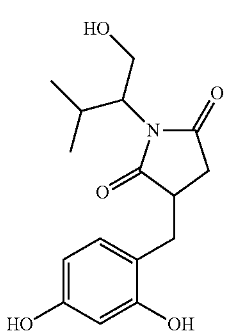 [SMILES: CC(C)C(CO)N1C(=O)CC(Cc2ccc(O)cc2O)C1=O] | 3-(2,4-dihydroxybenzyl)-1-(1-hydroxy-3-methylbutan-2-yl)pyrrolidine-2,5-dione |

-continued

| No. | Structure | Chemical name |
|---|---|---|
| 17 | 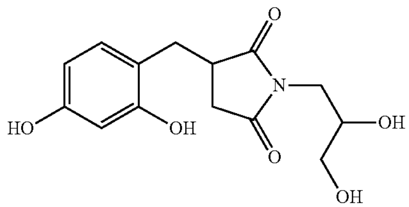 [SMILES: O=C1CC(Cc2ccc(O)cc2O)C(=O)N1CC(O)CO] | 3-(2,4-dihydroxybenzyl)-1-(2,3-dihydroxypropyl)pyrrolidine-2,5-dione |
| 18 | 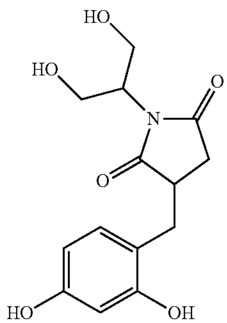 [SMILES: O=C1CC(Cc2ccc(O)cc2O)C(=O)N1C(CO)CO] | 3-(2,4-dihydroxybenzyl)-1-(1,3-dihydroxypropan-2-yl)pyrrolidine-2,5-dione |
| 19 | 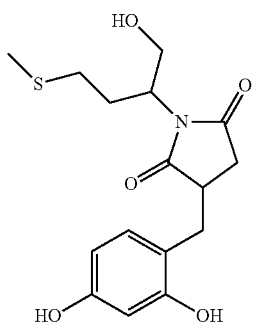 [SMILES: CSCCC(CO)N1C(=O)CC(Cc2ccc(O)cc2O)C1=O] | 3-(2,4-dihydroxybenzyl)-1-[1-hydroxy-4-(methylsulphanyl)butan-2-yl]pyrrolidine-2,5-dione |
| 20 | 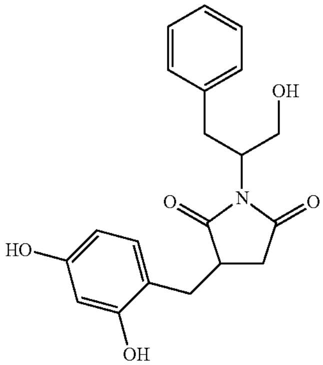 [SMILES: O=C1CC(Cc2ccc(O)cc2O)C(=O)N1C(CO)Cc1ccccc1] | 3-(2,4-dihydroxybenzyl)-1-(1-hydroxy-3-phenylpropan-2-yl)pyrrolidine-2,5-dione |
| 21 | 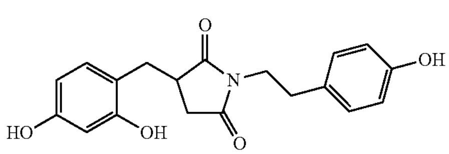 [SMILES: O=C1CC(Cc2ccc(O)cc2O)C(=O)N1CCc1ccc(O)cc1] | 3-(2,4-dihydroxybenzyl)-1-[2-(4-hydroxyphenyl)ethyl]pyrrolidine-2,5-dione |
| 22 | 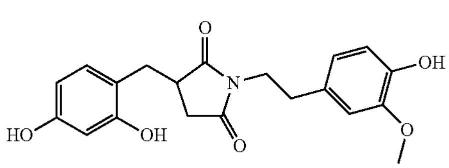 [SMILES: COc1cc(CCN2C(=O)CC(Cc3ccc(O)cc3O)C2=O)ccc1O] | 3-(2,4-dihydroxybenzyl)-1[2-(4-hydroxy-3-methoxyphenyl)ethyl]pyrrolidine-2,5-dione |

-continued

| No. | Structure | Chemical name |
|---|---|---|
| 23 | 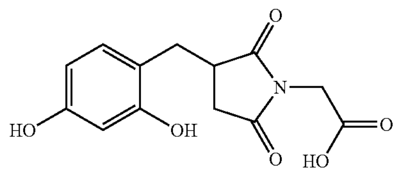 [SMILES: O=C(O)CN1C(=O)CC(Cc2ccc(O)cc2O)C1=O] | [3-(2,4-dihydroxybenzyl)-2,5-dioxopyrrolidin-1-yl]acetic acid |
| 24 | 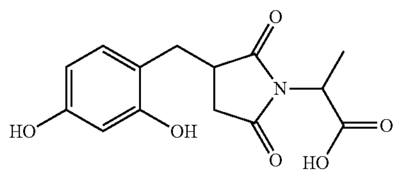 [SMILES: CC(C(=O)O)N1C(=O)CC(Cc2ccc(O)cc2O)C1=O] | 2-[3-(2,4-dihydroxybenzyl)-2,5-dioxopyrrolidin-1-yl]propanoic acid |
| 25 | 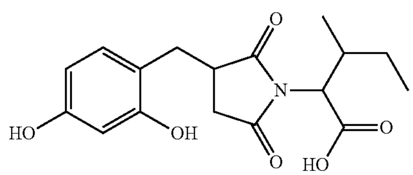 [SMILES: CCC(C)C(C(=O)O)N1C(=O)CC(Cc2ccc(O)cc2O)C1=O] | 2-[3-(2,4-dihydroxybenzyl)-2,5-dioxopyrrolidin-1-yl]-3-methylpentanoic acid |
| 26 | 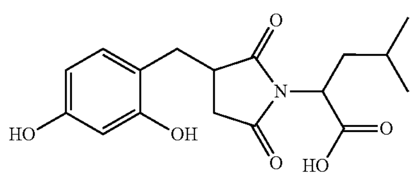 [SMILES: CC(C)CC(C(=O)O)N1C(=O)CC(Cc2ccc(O)cc2O)C1=O] | 2-[3-(2,4-dihydroxybenzyl)-2,5-dioxopyrrolidin-1-yl]-4-methylpentanoic acid |
| 27 | 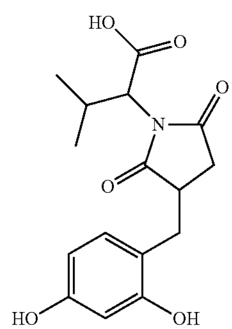 [SMILES: CC(C)C(C(=O)O)N1C(=O)CC(Cc2ccc(O)cc2O)C1=O] | 2-[3-(2,4-dihydroxybenzyl)-2,5-dioxopyrrolidin-1-yl]-3-methylbutanoic acid |
| 28 | 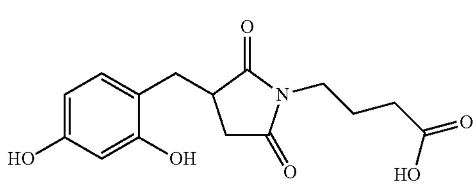 [SMILES: O=C(O)CCCN1C(=O)CC(Cc2ccc(O)cc2O)C1=O] | 4-[3-(2,4-dihydroxybenzyl)-2,5-dioxopyrrolidin-1-yl]butanoic acid |
| 29 | 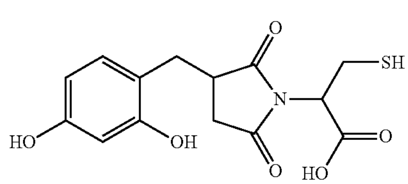 [SMILES: O=C(O)C(CS)N1C(=O)CC(Cc2ccc(O)cc2O)C1=O] | 2-[3-(2,4-dihydroxybenzyl)-2,5-dioxopyrrolidin-1-yl]-3-sulphanylpropanoic acid |

| No. | Structure | Chemical name |
|---|---|---|
| 30 | 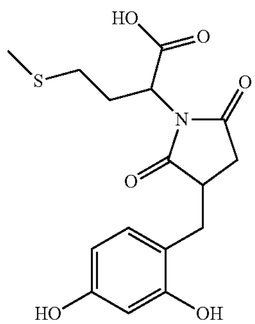 [SMILES: CSCCC(C(=O)O)N1C(=O)CC(Cc2ccc(O)cc2O)C1=O] | 2-[3-(2,4-dihydroxybenzyl)-2,5-dioxopyrrolidin-1-yl]-4-(methylsulphanyl)butanoic acid |
| 31 | 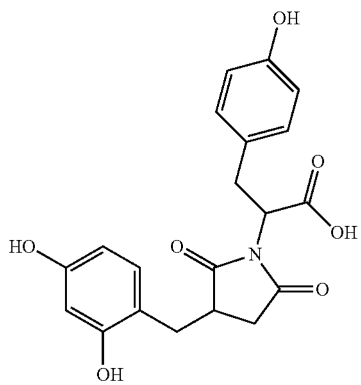 [SMILES: O=C(O)C(Cc1ccc(O)cc1)N1C(=O)CC(Cc2ccc(O)cc2O)C1=O] | 2-[3-(2,4-dihydroxybenzyl)-2,5-dioxopyrrolidin-1-yl]-3-(4-hydroxyphenyl)propanoic acid |
| 32 | 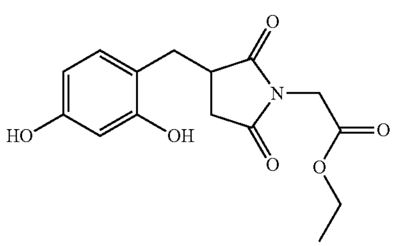 [SMILES: CCOC(=O)CN1C(=O)CC(Cc2ccc(O)cc2O)C1=O] | ethyl [3-(2,4-dihydroxybenzyl)-2,5-dioxopyrrolidin-1-yl]acetate |
| 33 | 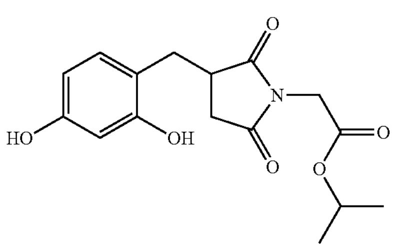 [SMILES: CC(C)OC(=O)CN1C(=O)CC(Cc2ccc(O)cc2O)C1=O] | isopropyl [3-(2,4-dihydroxybenzyl)-2,5-dioxopyrrolidin-1-yl]acetate |
| 34 | 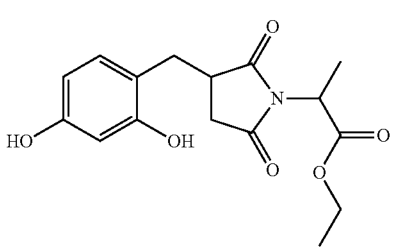 [SMILES: CCOC(=O)C(C)N1C(=O)CC(Cc2ccc(O)cc2O)C1=O] | ethyl 2-[3-(2,4-dihydroxybenzyl)-2,5-dioxopyrrolidin-1-yl]propanoate |

-continued
| No. | Structure | Chemical name |
|---|---|---|
| 35 | 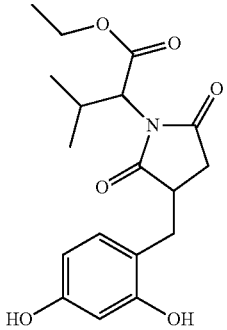 | ethyl 2-[3-(2,4-dihydroxybenzyl)-2,5-dioxopyrrolidin-1-yl]-3-methylbutanoate |
| 36 | 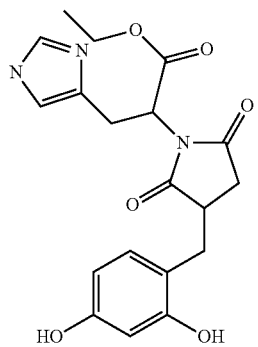 [SMILES: CCOC(=O)C(Cc1c[nH]cn1)N1C(=O)CC(Cc2ccc(O)cc2O)C1=O] | ethyl 2-[3-(2,4-dihydroxybenzyl)-2,5-dioxopyrrolidin-1-yl]-3-(1H-imidazol-4-yl)propanoate |
| 37 | 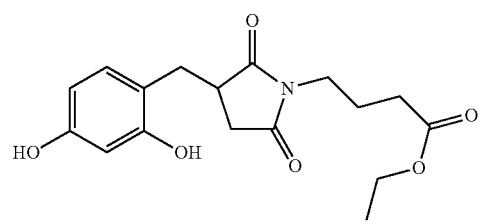 [SMILES: CCOC(=O)CCCN1C(=O)CC(Cc2ccc(O)cc2O)C1=O] | ethyl 4-[3-(2,4-dihydroxybenzyl)-2,5-dioxopyrrolidin-1-yl]butanoate |
| 38 | 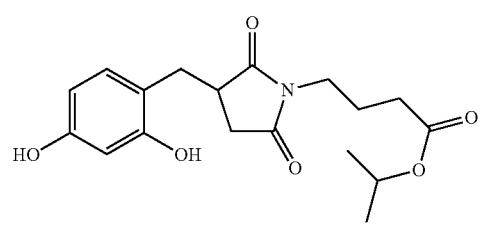 [SMILES: CC(C)OC(=O)CCCN1C(=O)CC(Cc2ccc(O)cc2O)C1=O] | isopropyl 4-[3-(2,4-dihydroxybenzyl)-2,5-dioxopyrrolidin-1-yl]butanoate |
| 39 | 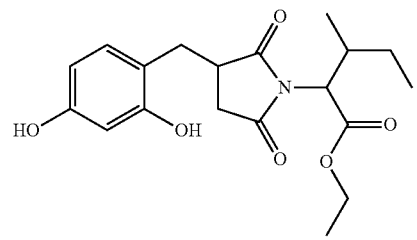 [SMILES: CCOC(=O)C(C(C)CC)N1C(=O)CC(Cc2ccc(O)cc2O)C1=O] | ethyl 2-[3-(2,4-dihydroxybenzyl)-2,5-dioxopyrrolidin-1-yl]-3-methylpentanoate |

-continued

| No. | Structure | Chemical name |
|---|---|---|
| 40 | 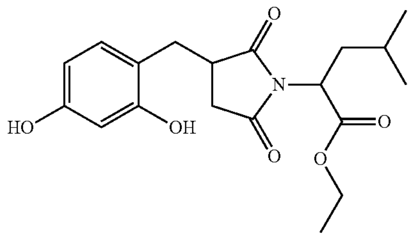 [SMILES: CCOC(=O)C(CC(C)C)N1C(=O)CC(Cc2ccc(O)cc2O)C1=O] | ethyl 2-[3-(2,4-dihydroxybenzyl)-2,5-dioxopyrrolidin-1-yl]-4-methylpentanoate |
| 41 | 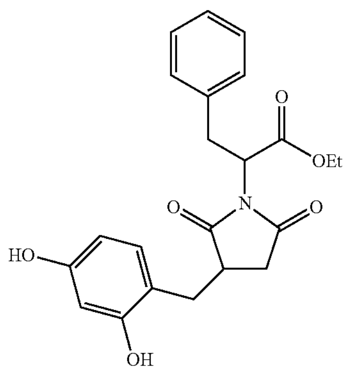 [SMILES: CCOC(=O)C(Cc1ccccc1)N1C(=O)CC(Cc2ccc(O)cc2O)C1=O] | ethyl 2-[3-2,4-dihydroxybenzyl 2,5-dioxopyrrolidin-1-yl]-3-phenylpropanoate |
| 42 | 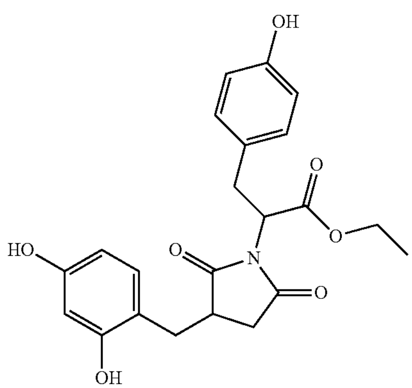 [SMILES: CCOC(=O)C(Cc1ccc(O)cc1)N1C(=O)CC(Cc2ccc(O)cc2O)C1=O] | ethyl 2-[3-(2,4-dihydroxybenzyl)-2,5-dioxopyrrolidin-1-yl]-3-(4-hydroxyphenyl)propanoate |
| 43 | 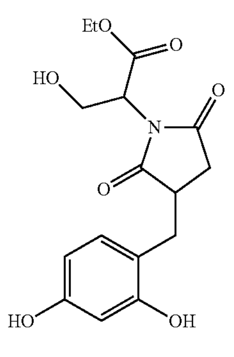 [SMILES: CCOC(=O)C(CO)N1C(=O)CC(Cc2ccc(O)cc2O)C1=O] | ethyl 2-[3-(2,4-dihydroxybenzyl)-2,5-dioxopyrrolidin-1-yl]-3-hydroxypropanoate |
| 44 | 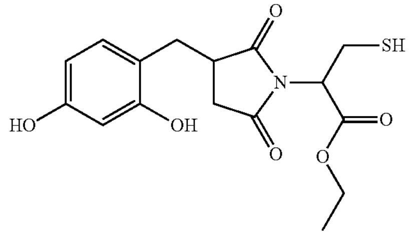 [SMILES: CCOC(=O)C(CS)N1C(=O)CC(Cc2ccc(O)cc2O)C1=O] | ethyl 2-[3-(2,4-dihydroxybenzyl)-2,5-dioxopyrrolidin-1-yl]-3-sulphanylpropanoate |

-continued

| No. | Structure | Chemical name |
|---|---|---|
| 45 | 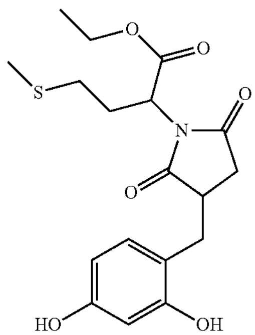 [SMILES: CCOC(=O)C(CCSC)N1C(=O)CC(Cc2ccc(O)cc2O)C1=O] | ethyl 2-[3-(2,4-dihydroxybenzyl)-2,5-dioxopyrrolidin-1-yl]-4-(methylsulphanyl)butanoate |
| 46 | 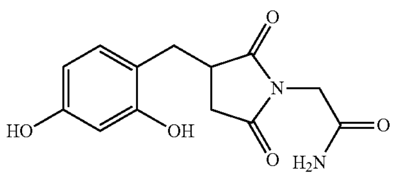 [SMILES: NC(=O)CN1C(=O)CC(Cc2ccc(O)cc2O)C1=O] | 2-[3-(2,4-dihydroxybenzyl)-2,5-dioxopyrrolidin-1-yl]acetamide |
| 47 | 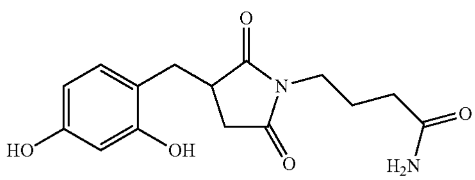 [SMILES: NC(=O)CCCN1C(=O)CC(Cc2ccc(O)cc2O)C1=O] | 4-[3-(2,4-dihydroxybenzyl)-2,5-dioxopyrrolidin-1-yl]butanamide |
| 48 | 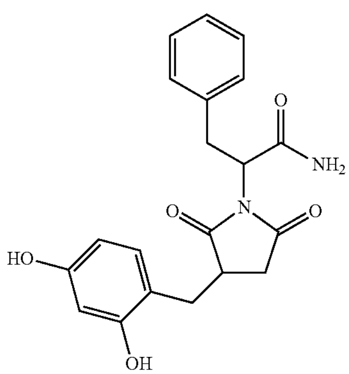 [SMILES: NC(=O)C(Cc1ccccc1)N1C(=O)CC(Cc2ccc(O)cc2O)C1=O] | 2-[3-(2,4-dihydroxybenzyl)-2,5-dioxopyrrolidin-1-yl]-3-phenylpropanamide |
| 49 | 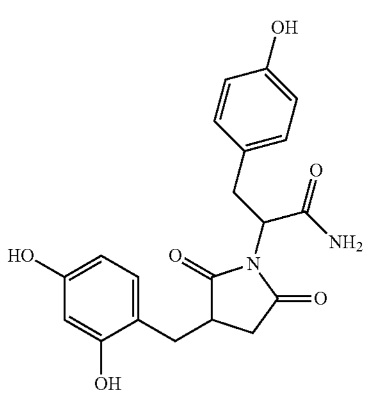 [SMILES: NC(=O)C(Cc1ccc(O)cc1)N1C(=O)CC(Cc2ccc(O)cc2O)C1=O] | 2-[3-(2,4-dihydroxybenzyl)-2,5-dioxopyrrolidin-1-yl]-3-(4-hydroxyphenyl)propanamide |

-continued

| No. | Structure | Chemical name |
|---|---|---|
| 50 | 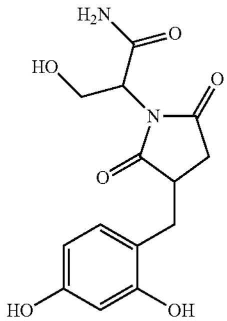 [SMILES: NC(=O)C(CO)N1C(=O)CC(Cc2ccc(O)cc2O)C1=O] | 2-[3-(2,4-dihydroxybenzyl)-2,5-dioxopyrrolidin-1-yl]-3-hydroxypropanamide |
| 51 | 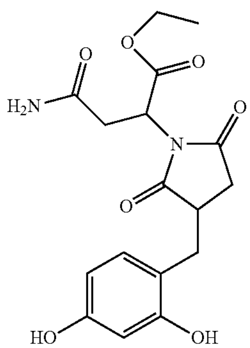 [SMILES: CCOC(=O)C(CC(N)=O)N1C(=O)CC(Cc2ccc(O)cc2O)C1=O] | ethyl 4-amino-2-[3-(2,4-dihydroxybenzyl)-2,5-dioxopyrrolidin-1-yl]-4-oxobutanoate |
| 52 | 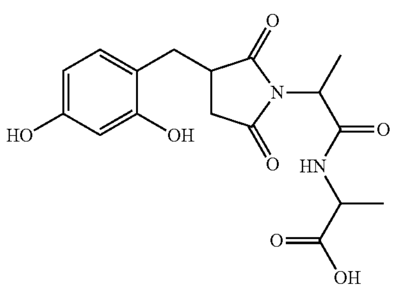 [SMILES: CC(NC(=O)C(C)N1C(=O)CC(Cc2ccc(O)cc2O)C1=O)C(=O)O] | N-{2-[3-(2,4-dihydroxybenzyl)-2,5-dioxopyrrolidin-1-yl]propanoyl}alanine |
| 53 | 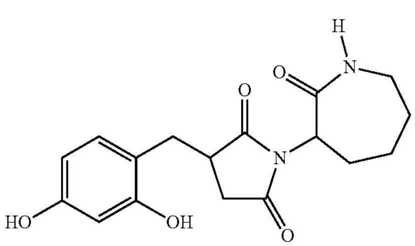 [SMILES: O=C1NCCCCC1N1C(=O)CC(Cc2ccc(O)cc2O)C1=O] | 3-(2,4-dihydroxybenzyl)-1-(2-oxoazepan-3-yl)pyrrolidine-2,5-dione |
| 54 | 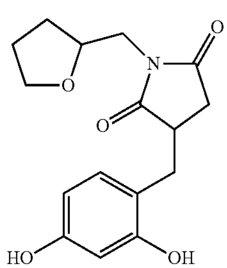 [SMILES: O=C1CC(Cc2ccc(O)cc2O)C(=O)N1CC1CCCO1] | 3-(2,4-dihydroxybenzyl)-1-(tetrahydrofuran-2-ylmethyl)pyrrolidine-2,5-dione |

-continued

| No. | Structure | Chemical name |
|---|---|---|
| 55 | 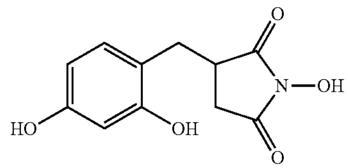 [SMILES: O=C1CC(Cc2ccc(O)cc2O)C(=O)N1O] | 3-(2,4-dihydroxybenzyl)-1-hydroxypyrrolidine-2,5-dione |
| 56 | 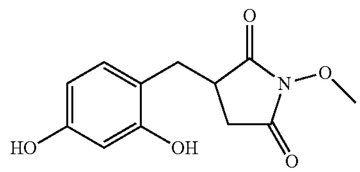 [SMILES: CON1C(=O)CC(Cc2ccc(O)cc2O)C1=O] | 3-(2,4-dihydroxybenzyl)-1-methoxypyrrolidine-2,5-dione |
| 57 | 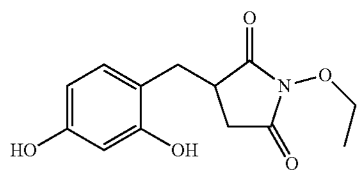 [SMILES: CCON1C(=O)CC(Cc2ccc(O)cc2O)C1=O] | 3-(2,4-dihydroxybenzyl)-1-ethoxypyrrolidine-2,5-dione |
| 58 | 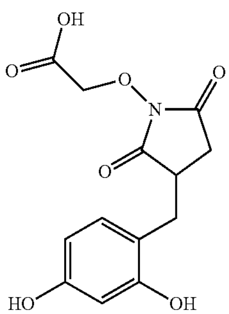 [SMILES: O=C(O)CON1C(=O)CC(Cc2ccc(O)cc2O)C1=O] | {[3-(2,4-dihydroxybenzyl)-2,5-dioxopyrrolidin-1-yl]oxy}acetic acid |
| 59 | 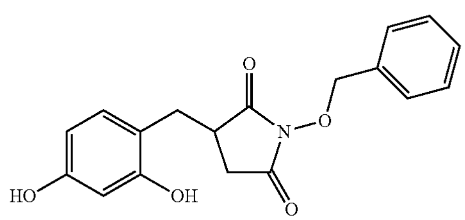 [SMILES: O=C1CC(Cc2ccc(O)cc2O)C(=O)N1OCc1ccccc1] | 3-(2,4-dihydroxybenzyl)-1-benzyloxypyrrolidine-2,5-dione |
| 60 | 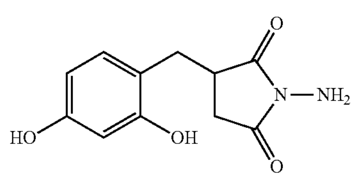 [SMILES: NN1C(=O)CC(Cc2ccc(O)cc2O)C1=O] | 1-amino-3-(2,4-dihydroxybenzyl)pyrrolidine-2,5-dione |
| 61 | 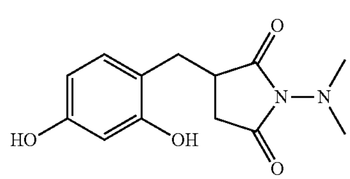 [SMILES: CN(C)N1C(=O)CC(Cc2ccc(O)cc2O)C1=O] | 3-(2,4-dihydroxybenzyl)-1-(dimethylamino)pyrrolidine-2,5-dione |
| 62 | 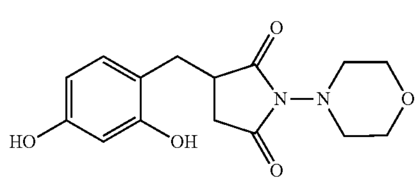 [SMILES: O=C1CC(Cc2ccc(O)cc2O)C(=O)N1N1CCOCC1] | 3-(2,4-dihydroxybenzyl)-1-(morpholin-4-yl)pyrrolidine-2,5-dione |

-continued
| No. | Structure | Chemical name |
|---|---|---|
| 63 | 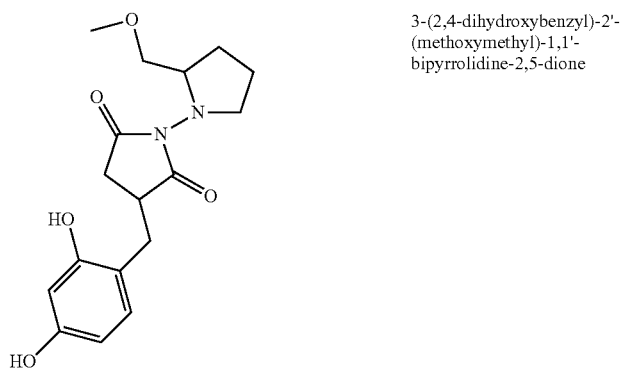 | 3-(2,4-dihydroxybenzyl)-2'-(methoxymethyl)-1,1'-bipyrrolidine-2,5-dione |
| 64 | 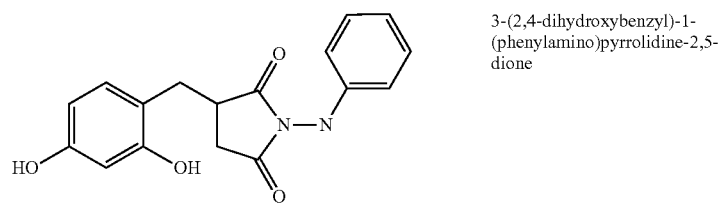 | 3-(2,4-dihydroxybenzyl)-1-(phenylamino)pyrrolidine-2,5-dione |
| 65 | 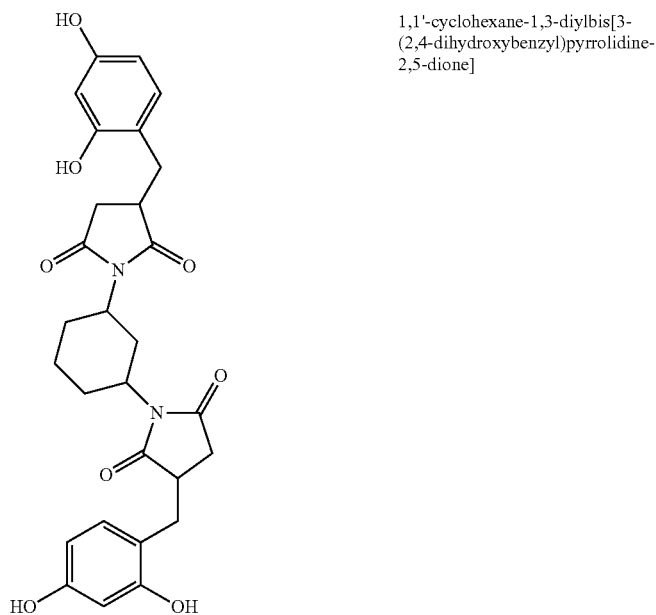 | 1,1'-cyclohexane-1,3-diylbis[3-(2,4-dihydroxybenzyl)pyrrolidine-2,5-dione] |

| No. | Structure | Chemical name |
|---|---|---|
| 66 | 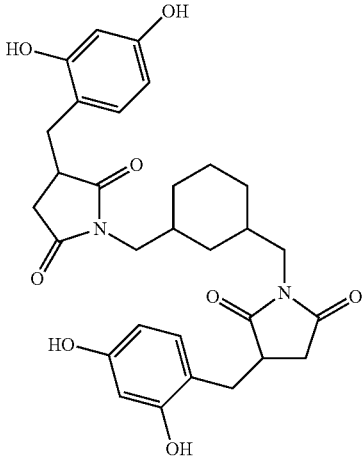 [SMILES: O=C1CC(Cc2ccc(O)cc2O)C(=O)N1CC1CCCC(CN2C(=O)CC(Cc3ccc(O)cc3O)C2=O)C1] | 1,1'-(cyclohexane-1,3-diyldimethanediyl)bis[3-(2,4-dihydroxybenzyl)pyrrolidine-2,5-dione] |
| 67 | 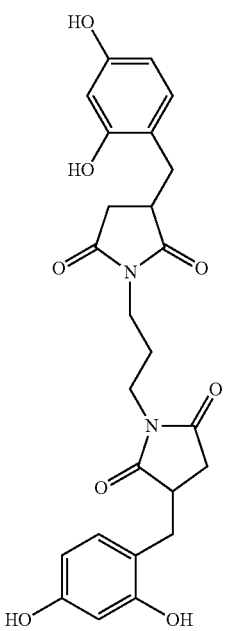 [SMILES: O=C1CC(Cc2ccc(O)cc2O)C(=O)N1CCCN1C(=O)CC(Cc2ccc(O)cc2O)C1=O] | 1,1'-propane-1,3-diylbis[3-(2,4-dihydroxybenzyl)pyrrolidine-2,5-dione] |

| No. | Structure | Chemical name |
|---|---|---|
| 68 | 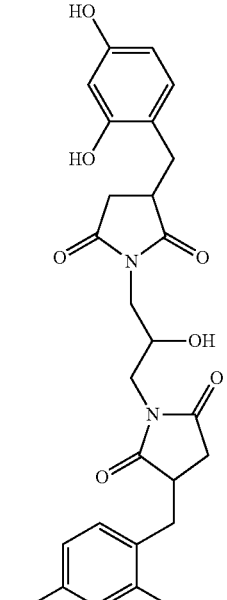 | 1,1'-(2-hydroxypropane-1,3-diyl)bis[3-(2,4-dihydroxybenzyl)pyrrolidine-2,5-dione] |
| 69 | 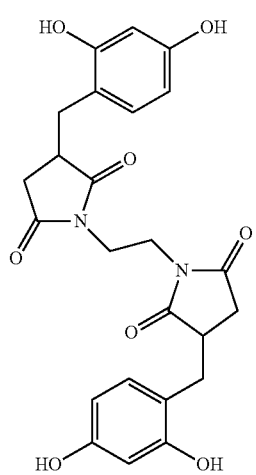 [SMILES: O=C1CC(Cc2ccc(O)cc2O)C(=O)N1CCN1C(=O)CC(Cc2ccc(O)cc2O)C1=O] | 1,1'-ethane-1,2-diylbis[3-(2,4-dihydroxybenzyl)pyrrolidine-2,5-dione] |
| 70 | 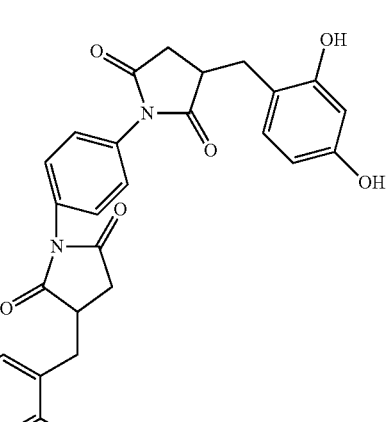 | 1,1'-benzene-1,4-diylbis[3-(2,4-dihydroxybenzyl)pyrrolidine-2,5-dione] |

-continued

| No. | Structure | Chemical name |
|---|---|---|
| 71 | 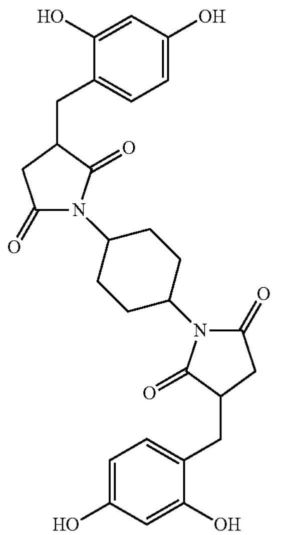 [SMILES: O=C1CC(Cc2ccc(O)cc2O)C(=O)N1C1CCC(N2C(=O)CC(Cc3ccc(O)cc3O)C2=O)CC1] | 1,1'-cyclohexane-1,4-diylbis[3-(2,4-dihydroxybenzyl)pyrrolidine-2,5-dione] |
| 72 | 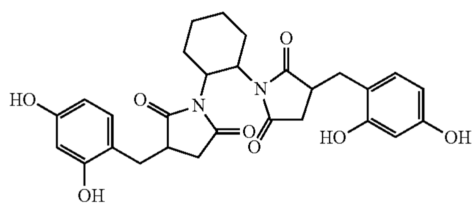 [SMILES: O=C1CC(Cc2ccc(O)cc2O)C(=O)N1C1CCCCC1N1C(=O)CC(Cc2ccc(O)cc2O)C1=O] | 1,1'-cyclohexane-1,2-diylbis[3-(2,4-dihydroxybenzyl)pyrrolidine-2,5-dione] |
| 73 | | ethyl 2,6-bis[3-(2,4-dihydroxybenzyl)-2,5-dioxopyrrolidin-1-yl]hexanoate | and also their salts, their solvates, their optical isomers and their racemates.

Among these compounds, more particular preference is given to the following compounds:

| No. | Structure | Chemical name |
|---|---|---|
| 2 | 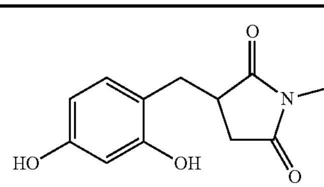 | 3-(2,4-dihydroxybenzyl)-1-methylpyrrolidine-2,5-dione |
| 3 | 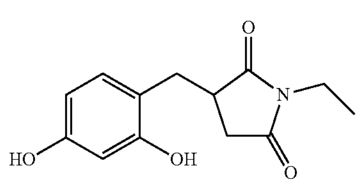 [SMILES: CCN1C(=O)CC(Cc2ccc(O)cc2O)C1=O] | 3-(2,4-dihydroxybenzyl)-1-ethylpyrrolidine-2,5-dione |

-continued
| No. | Structure | Chemical name |
|---|---|---|
| 4 | 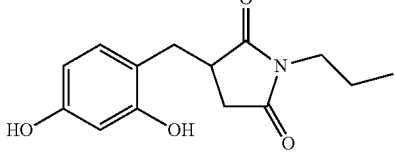 | 3-(2,4-dihydroxybenzyl)-1-propylpyrrolidine-2,5-dione |
| 5 | 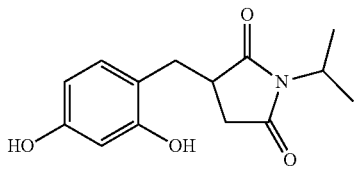 [SMILES: CC(C)N1C(=O)CC(Cc2ccc(O)cc2O)C1=O] | 3-(2,4-dihydroxybenzyl)-1-isopropylpyrrolidine-2,5-dione |
| 6 | 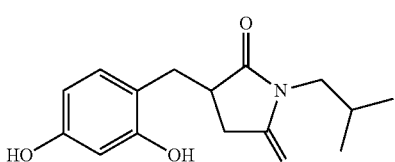 | 3-(2,4-dihydroxybenzyl)-1-isobutylpyrrolidine-2,5-dione |
| 7 | 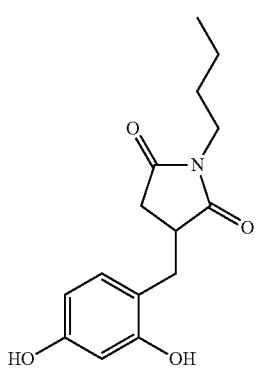 [SMILES: CCCCN1C(=O)CC(Cc2ccc(O)cc2O)C1=O] | 3-(2,4-dihydroxybenzyl)-1-butylpyrrolidine-2,5-dione |
| 8 | 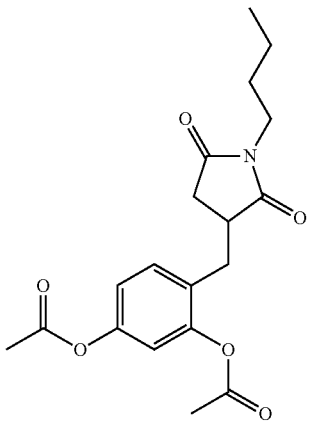 [SMILES: CCCCN1C(=O)CC(Cc2ccc(OC(C)=O)cc2OC(C)=O)C1=O] | 4-[(1-butyl-2,5-dioxopyrrolidin-3-yl)methyl]benzene-1,3-diyl diacetate |
| 32 | 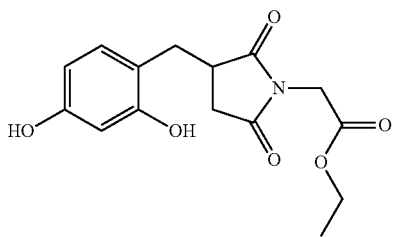 [SMILES: CCOC(=O)CN1C(=O)CC(Cc2ccc(O)cc2O)C1=O] | ethyl [3-(2,4-dihydroxybenzyl)-2,5-dioxopyrrolidin-1-yl]acetate |

-continued

| No. | Structure | Chemical name |
|---|---|---|
| 33 | 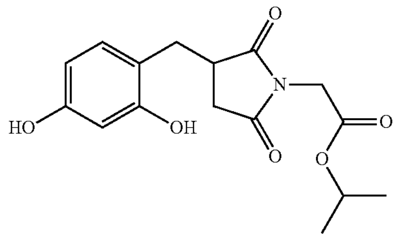 | isopropyl [3-(2,4-dihydroxybenzyl)-2,5-dioxopyrrolidin-1-yl]acetate |
| 34 | 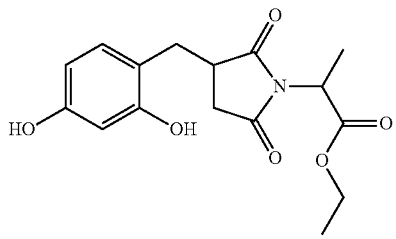 [SMILES: CCOC(=O)C(C)N1C(=O)CC(Cc2ccc(O)cc2O)C1=O] | ethyl 2-[3-(2,4-dihydroxybenzyl)-2,5-dioxopyrrolidin-1-yl]propanoate |
| 35 | | ethyl 2-[3-(2,4-dihydroxybenzyl)-2,5-dioxopyrrolidin-1-yl]-3-methylbutanoate | and also their salts, their solvates, their optical isomers and their racemates.

The invention likewise provides a process for preparing the above-described compounds of formula (I), which comprises the following steps:

A) reacting resorcinol (A1) with itaconic acid (B) or its anhydride (B') or one of its esters of formula (B1)

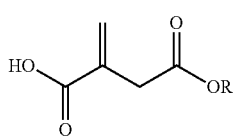
B1 in which R denotes H or a $C_3$-$C_6$ branched or $C_1$-$C_6$ linear alkyl group, to form a compound C of formula (III), then B) reacting the compound C of formula (III), optionally in activated form, with a compound of formula (IV) A-NH$_2$, in which A has the same meaning described above for the compounds of formula (I), optionally in the presence of a basic or acidic catalyst, optionally with heating to a temperature of between 15° C. and 20° C., C) optionally carrying out an acetylation reaction.

The invention likewise provides the compounds C of formula (III):

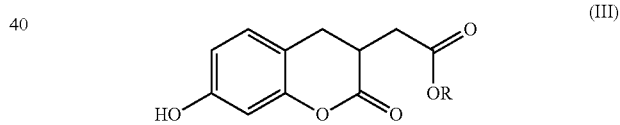
(III)

in which R denotes H or a $C_3$-$C_6$ branched or $C_1$-$C_6$ linear alkyl group.

These compounds of formula (III) are synthesis intermediates in the preparation process described above.

The compounds of formula (I) may thus be obtained in accordance with reaction scheme I below:

Scheme I

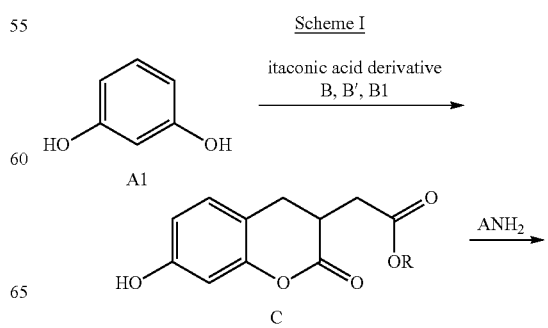

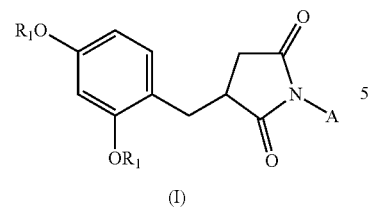

(I)

A) by reacting resorcinol in the presence of itaconic acid (B) or its anhydride (B') or one of its esters of formula (B1) described above, to give the compound C (III) (schemes II and III), particularly in the presence of an organic solvent which may be selected from toluene, tetrahydrofuran, heptane, isooctane, methyltetrahydrofuran, methyl ethyl ketone, methyl isobutyl ketone, dioxane, ethyl acetate, isopropyl acetate, isododecane and mixtures thereof, particularly at a temperature of between 15 and 200° C., optionally in the presence of a catalyst (acidic or basic) as described in the following publications: Synthesis of 7-hydroxycoumarins by Pechmann reaction using Nafion resin/silica nanocomposites as catalysts: Laufer M C, Hausmann H, Hölderich W F, J of catalysis, 2003, 218, 315-320; Synthesis of 7-hydroxycoumarins catalysed by solid acid catalysts: Hoefnagel A, Gunnewegh E, Downing R, van Bekkum H, J Chem Soc Chem Commun, 1995, 225-226; more particularly in the presence of an acidic catalyst such as methanesulphonic acid, triflic acid, para-toluenesulphonic acid and sulphonic resins as Dowex® resins or Amberlyst® resins (sold by Aldrich).

Scheme II

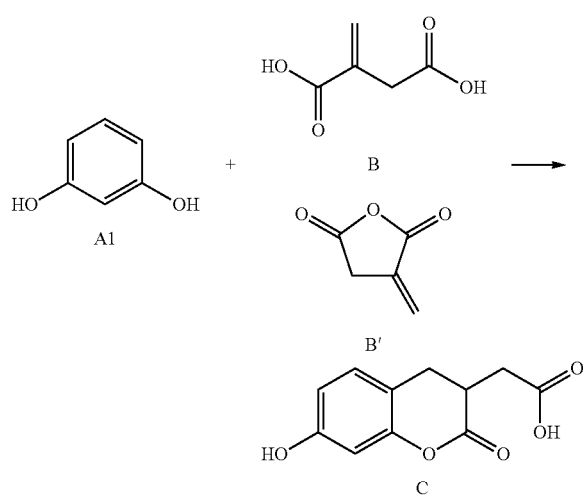

Scheme III

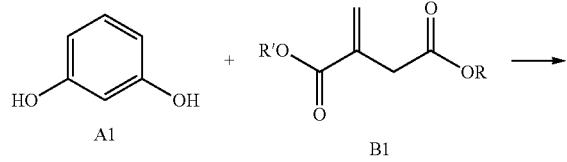

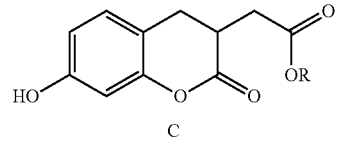

C

B) then reacting the compound C (III) with a compound of formula (IV) A-NH$_2$, where A has the same meaning described above for the compounds of formula (I), optionally in the presence of an organic solvent, more particularly tetrahydrofuran, dioxane, dimethylformamide, dimethyl sulphoxide;

optionally in the presence of a catalyst selected from Lewis or Bronsted acid catalysts or basic catalysts, such as potassium carbonate, triethylamine or diisopropylethylamine;

optionally with heating at a temperature of between 15° C. and 200° C., more particularly between 30° C. and 150° C.

This gives the compounds (I) for which $R_1$=H (schemes I and V).

C) and optionally carrying out an acetylation reaction to give the compounds (I) for which $R_1$=acetyl.

The compounds B1 for which R is other than H may be obtained conventionally by selective esterification in acidic medium of itaconic acid with one or more alcohols of formula ROH (where R has the meanings described above), as described in the literature (Selective esterification of non-conjugated carboxylic acids in the presence of conjugated or aromatic carboxylic acids over active carbon supported methanesulphonic acid; Feng, Ze Wang; Zhao, Xin Qi; Bi, Hua, Science in China, Series B: Chemistry (2008), 1(10), 990-992/An efficient and regiospecific esterification of dioic acids using PTSA; Devi, A. Rama; Rajaram, S. Indian Journal of Chemistry, Section B: Organic Chemistry Including Medicinal Chemistry (2000), 39B(4), 294-296/A simple method for the preparation of monomethyl esters of dicarboxylic acids by selective esterification of the nonconjugated carboxyl group in the presence of an aromatic or conjugated carboxyl group; Ram, Ram N.; Meher, Nabin Kumar; Journal of Chemical Research, Synopses (2000), (6), 282-283.).

According to one particular embodiment of step (B) of the synthesis process, when the group R of the compound C denotes H, the compound of formula (I) may be obtained by activating the acid C in accordance with known techniques for activating acids, described in particular in Comprehensive Organic Transformation by R. Larock, published by Wiley VCH, in the chapter Interconversion of nitriles, carboxylic acids and derivatives.

Acid activation techniques include the following:
the intermediate formation of acid chloride (for example using thionyl or oxalyl chloride, or 1-chloro-N,N,2-trimethyl-1-propenamine),
the intermediate formation of mixed anhydride (for example using a $C_2$-$C_6$ alkyl chloroformate, such as isobutyl chloroformate (scheme IV), in the presence of a base such as, for example, triethylamine or diisopropylethylamine;
the intermediate formation of carbamimidate or of acylphosphonate (for example using carbodiimides or diethyl cyanophosphate; Phosphorus in organic synthesis-XI, Amino acids and peptides-XXI, Reaction of diethyl phosphorocyanidate with carboxylic acids. A new synthesis of carboxylic esters and amides, Tetrahedron, 32, 1976, 2211-2217).

Scheme IV

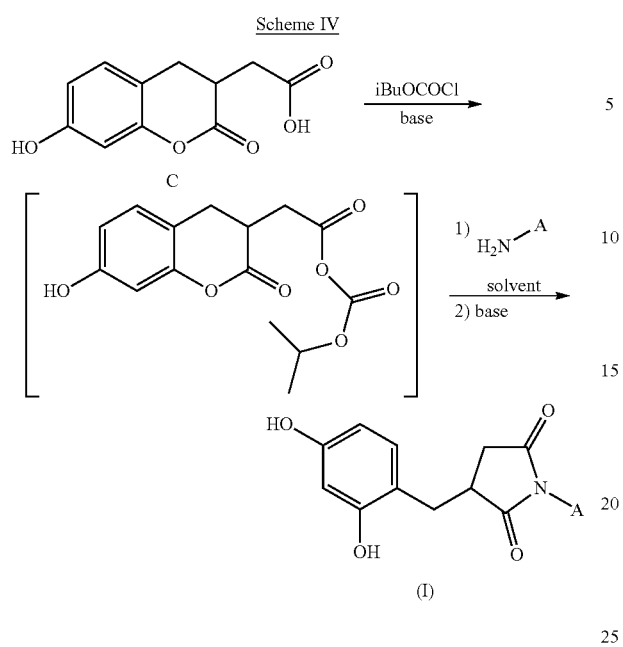

Scheme V

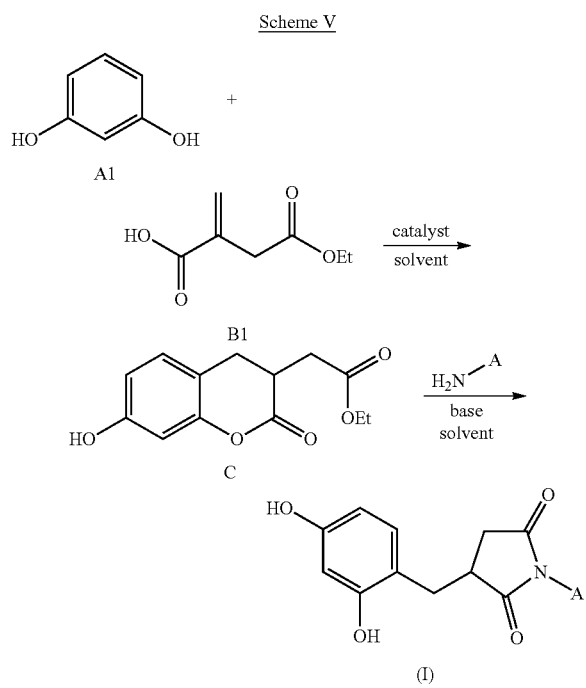

The compounds of formula (I) for which $R_1$ denotes an acetyl group may be obtained by acetylating compounds of formula (I) for which $R_1$=H.

The acetylation reaction may be carried out with acetic anhydride or acetyl chloride, especially in the presence of an aprotic solvent such as toluene, pyridine or tetrahydrofuran.

The acetylation reaction may be selective, by employing protective groups on the functions which are not to be acetylated, then carrying out a deprotection reaction, according to the known techniques of organic synthesis.

All of these steps may also employ protection/deprotection strategies which are in common use in organic chemistry, as compiled in the work "Protecting Groups in Organic Synthesis", Greene, Wuts, Wiley Interscience.

According to one particular embodiment of the preparation process, the compounds of formula (I) for which A denotes a group of formula (II) as described above may be prepared by reacting the compound C (III) in the presence of a diamine of formula (V) $H_2N$—X—$NH_2$ according to the reaction scheme below:

Scheme VI

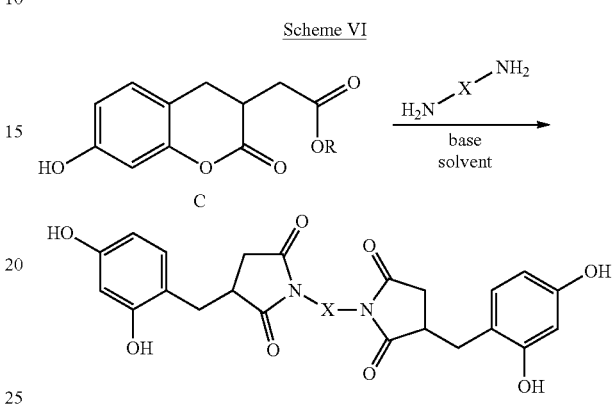

The reaction may take place in the presence or absence of a solvent, more particularly tetrahydrofuran, dioxane, dimethylformamide or dimethylsulphoxide.

The reaction may take place in the presence of a catalyst selected from Lewis or Bronsted acid catalysts or basic catalysts, such as potassium carbonate, triethylamine and diisopropylethylamine.

The reaction may be carried out at a temperature of between 0° C. and 200° C., more particularly between 30° C. and 150° C.

The compounds of formula (I) according to the invention are employed especially in the cosmetics sector.

The composition according to the invention comprises, in a physiologically acceptable medium, a compound of formula (I) as described above.

A physiologically acceptable medium is a medium which is compatible with the keratin materials of human beings such as the skin of the face or body, the lips, the mucous membranes, the eyelashes, the nails, the scalp and/or the hair.

The compound (I) may be present in the composition according to the invention in an amount which may be between 0.01% and 10% by weight, preferably between 0.1% to 5% by weight, in particular from 0.5% to 3% by weight, relative to the total weight of the composition.

The composition according to the invention is advantageously a cosmetic composition: it may comprise adjuvants which are commonly employed in the cosmetics sector.

Included in particular are water; organic solvents, especially $C_2$-$C_6$ alcohols; oils, especially hydrocarbon oils, silicone oils; waxes, pigments, fillers, dyes, surfactants, emulsifiers; active cosmetic ingredients, UV filters, polymers, thickeners, preservatives, fragrances, bactericides, odour absorbers and antioxidants.

These optional cosmetic adjuvants may be present in the composition in a proportion of 0.001% to 80% by weight, in particular 0.1% to 40% by weight, relative to the total weight of the composition. In any event, these adjuvants, and also their proportions, will be selected by the skilled person such that the advantageous properties of the compounds according to the invention are not, or not substantially, adversely affected by the intended addition.

Active agents which it will be advantageous to introduce into the composition according to the invention are at least one compound selected from desquamating agents; calmatives, organic or inorganic light stabilizers, moisturizers; depigmenting or propigmenting agents; anti-glycation agents; NO-synthase inhibitors; agents stimulating the synthesis of dermal or epidermal macromolecules and/or preventing their degradation; agents stimulating fibroblast and/or keratinocyte proliferation or stimulating keratinocyte differentiation; muscle relaxants and/or dermal decontractants; tensioning agents; anti-pollution agents and/or free-radical scavengers; agents acting on the microcirculation; agents acting on the energy metabolism of the cells; and mixtures thereof.

Examples of such additional compounds are: retinol and derivatives thereof such as retinyl palmitate; ascorbic acid and derivatives thereof such as magnesium ascorbyl phosphate and ascorbyl glucoside; tocopherol and derivatives thereof such as tocopheryl acetate; nicotinic acid and precursors thereof such as nicotinamide; ubiquinone; glutathione and precursors thereof such as L-2-oxothiazolidine-4-carboxylic acid; plant extracts and especially plant proteins and hydrolysates thereof, and also plant hormones; marine extracts such as algal extracts; bacterial extracts; sapogenins such as diosgenin and wild yam extracts containing them; ceramides; hydroxy acids such as salicylic acid and 5-n-octanoylsalicylic acid; resveratrol; oligopeptides and pseudodipeptides and acyl derivatives thereof; manganese and magnesium salts, in particular the gluconates; and mixtures thereof.

The term "desquamating agent" means any compound capable of acting:
either directly on desquamation by promoting exfoliation, such as β-hydroxy acids, in particular salicylic acid and derivatives thereof (including 5-n-octanoylsalicylic acid); α-hydroxy acids, such as glycolic acid, citric acid, lactic acid, tartaric acid, malic acid or mandelic acid; urea; gentisic acid; oligofucoses; cinnamic acid; *Saphora japonica* extract; resveratrol;
or on the enzymes involved in the desquamation or degradation of corneodesmosomes, glycosidases, stratum corneum chymotryptic enzyme (SCCE) or other proteases (trypsin, chymotrypsin-like). These include agents for chelating mineral salts: EDTA; N-acyl-N, N'N'-ethylenediaminetriacetic acid; aminosulphonic compounds and in particular (N-2-hydroxyethylpiperazine-N-2-ethane)sulphonic acid (HEPES); 2-oxothiazolidine-4-carboxylic acid (procysteine) derivatives; derivatives of alpha-amino acids of glycine type (as described in EP-0 852 949, and also sodium methyl glycine diacetate sold by BASF under the trade name Trilon M); honey; sugar derivatives such as O-octanoyl-6-D-maltose and N-acetylglucosamine.

The desquamating agents are generally present in the composition according to the invention in proportions ranging from 0.01% to 15% by weight and preferably ranging from 0.1% to 10% by weight relative to the total weight of the composition.

Calmatives that may be used in the composition according to the invention include the following: pentacyclic triterpenes and extracts of plants (e.g.: *Glycyrrhiza glabra*) containing them, for instance β-glycyrrhetinic acid and salts and/or derivatives thereof (glycyrrhetinic acid monoglucuronide, stearyl glycyrrhetinate or 3-stearoyl-oxyglycyrrhetic acid), ursolic acid and its salts, oleanolic acid and its salts, betulinic acid and its salts, an extract of *Paeonia suffruticosa* and/or *lactiflora*, salicylic acid salts and in particular zinc salicylate, the phycosaccharides from the company Codif, an extract of *Laminaria saccharina*, canola oil, bisabolol and camomile extracts, allantoin, Sepivital EPC (phosphoric diester of vitamins E and C) from SEPPIC, omega-3 unsaturated oils such as musk rose oil, blackcurrant oil, ecchium oil, fish oil, plankton extracts, capryloylglycine, Seppicalm VG (sodium palmitoylproline and *Nymphea alba*) from SEPPIC, a *Pygeum* extract, an extract of *Boswellia serrata*, an extract of *Centipeda cunninghami*, an extract of *Helianthus annuus*, an extract of *Linum usitatissimum*, tocotrienols, extracts of *Cola nitida*, piperonal, an extract of clove, an extract of *Epilobium Angustifolium*, Aloe vera, an extract of *Bacopa monieri*, phytosterols, cortisone, hydrocortisone, indomethacin and betamethasone.

The calmatives are generally present in the composition according to the invention in proportions ranging from 0.01% to 15% by weight and preferably ranging from 0.1% to 10% by weight relative to the total weight of the composition.

The organic light stabilizers are selected especially from anthranilates; cinnamic derivatives; dibenzoylmethane derivatives; salicylic derivatives; camphor derivatives; triazine derivatives such as those described in patent applications U.S. Pat. No. 4,367,390, EP 863 145, EP 517 104, EP 570 838, EP 796 851, EP 775 698, EP 878 469, EP 933 376, EP 507 691, EP 507 692, EP 790 243, EP 944 624; benzophenone derivatives; β,β-diphenylacrylate derivatives; benzotriazole derivatives; benzalmalonate derivatives; benzimidazole derivatives; imidazolines; bis-benzazolyl derivatives as described in patents EP 669 323 and U.S. Pat. No. 2,463,264; p-aminobenzoic acid (PABA) derivatives; methylenebis(hydroxyphenylbenzotriazole) derivatives as described in patent applications U.S. Pat. Nos. 5,237,071, 5,166,355, GB 2 303 549, DE 197 26 184 and EP 893 119; screening polymers and screening silicones such as those described especially in patent application WO 93/04665; α-alkylstyrene-based dimers, such as those described in patent application DE 198 55 649.

The inorganic light stabilizers may be selected especially from pigments or nanopigments (average size of the primary particles: generally between 5 nm and 100 nm and preferably between 10 nm and 50 nm) of coated or uncoated metal oxides, for instance nanopigments of titanium oxide (amorphous or crystallized in rutile and/or anatase form), of iron oxide, of zinc oxide, of zirconium oxide or of cerium oxide, which are all well-known UV light stabilizers. Standard coating agents are, moreover, alumina and/or aluminium stearate. Such coated or uncoated metal oxide nanopigments are described in particular in patent applications EP 518 772 and EP 518 773.

The light stabilizers are generally present in the composition according to the invention in proportions ranging from 0.1% to 20% by weight and preferably ranging from 0.2% to 15% by weight relative to the total weight of the composition.

The composition according to the invention may be in any of the formulation forms normally used in the cosmetics sector, and especially in the form of an optionally gelled aqueous or aqueous-alcoholic solution, a dispersion, optionally a two-phase dispersion, of the lotion type, an oil-in-water or water-in-oil or multiple emulsion (for example W/O/W or O/W/O), an aqueous gel, a dispersion of oil in an aqueous phase with the aid of spherules, these spherules possibly being polymeric nanoparticles such as nanospheres and nanocapsules or, better still, lipid vesicles of ionic and/or nonionic type; aqueous or oily gels. These compositions are prepared according to the usual methods. According to this invention, a composition in the form of an emulsion, especially an oil-in-water emulsion, is preferably used.

The composition according to the invention may constitute a skincare composition, and especially a cleansing, protecting, treatment or care cream for the face, the hands, the feet, the major anatomical folds or the body (for example day creams, night creams, makeup-removing creams, foundation creams or antisun creams); a fluid foundation, a makeup-removing milk, a protective or care body milk or an antisun milk; or a skincare lotion, gel or mousse, such as a cleansing lotion.

The invention is illustrated in greater detail by the non-limiting examples that follow.

EXAMPLE 1

Synthesis of Compound 10

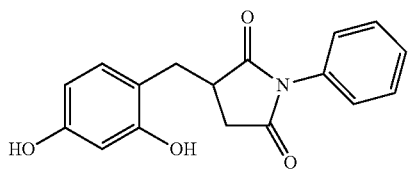

a) Synthesis of (7-hydroxy-2-oxo-3,4-dihydro-2H-chromen-3-yl)acetic acid (C1)

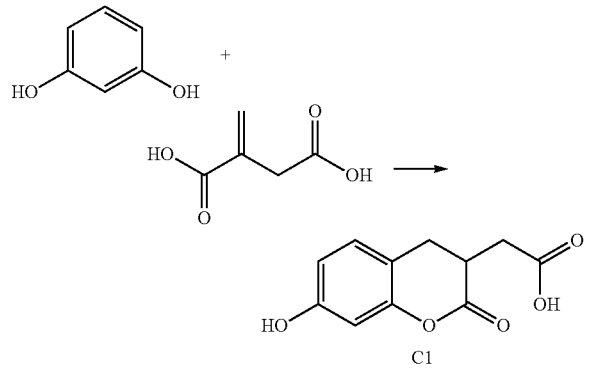

In a round-bottomed flask equipped with a Dean-Stark apparatus, 10 g of resorcinol and 11.8 g of itaconic acid were dissolved in 150 ml of a toluene/dioxane mixture (volume ratio 1/1) in the presence of Amberlyst 15 resin from Aldrich. The reaction mixture was heated at 100° C. for 3 hours. After cooling, the crude reaction product was filtered and the filtrate was concentrated under vacuum. The crude product was recrystallized hot from ethyl acetate. This gave 10 g of a white powder, which corresponds to the expected product (50% yield).

Melting point: 174-175° C.

b) Synthesis of Compound 10

A solution of 450 mg (2 mmol) of (7-hydroxy-2-oxo-3,4-dihydro-2H-chromen-3-yl)acetic acid (obtained according to step a) described above, in 15 ml of tetrahydrofuran (THF) was admixed with 223 mg (2.2 mmol) of triethylamine and 0.3 g (2.2 mmol) of isobutyl chloroformate. After reaction, this solution was added to 250 mg (2.2 mmol) of phenylamine (or aniline=amine A-NH$_2$ with A=phenyl) in 15 ml of THF. Following stirring at 20° C., the reaction mixture was concentrated under vacuum and then in THF at 40° C. in the presence of potassium carbonate after which, following filtration, concentration of the filtrate and purification by chromatography on a silica column, 0.18 g (30% yield) of the expected compound 10 was obtained.

The $^1$H NMR and mass spectra are in accordance with the structure of the expected product.

EXAMPLE 2

Synthesis of Compound 11

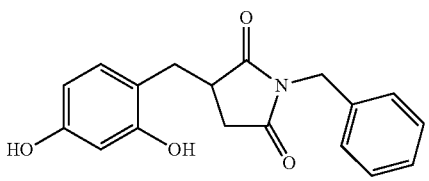 [SMILES: O=C1CC(Cc2ccc(O)cc2O)C(=O)N1Cc1ccccc1]

The procedure described in Example 1b) above was repeated, using benzylamine. This gave 0.35 g (56% yield) of compound 11.

The $^1$H NMR and mass spectra are in accordance with the structure of the expected product.

EXAMPLE 3

Synthesis of Compound 7

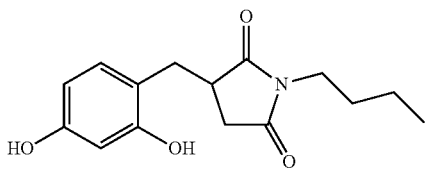 [SMILES: CCCCN1C(=O)CC(Cc2ccc(O)cc2O)C1=O]

a) Synthesis of ethyl (7-hydroxy-2-oxo-3,4-dihydro-2H-chromen-3-yl)acetate (C2)

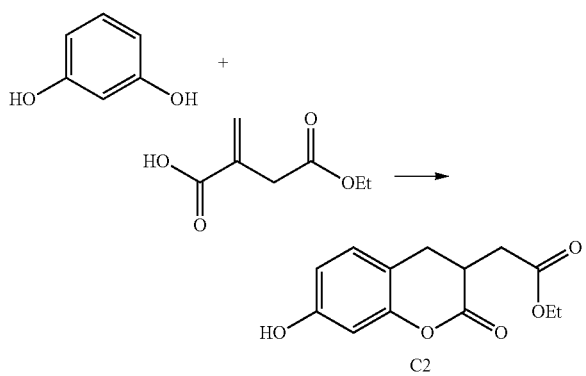

100 ml of toluene were admixed with 4.4 g (0.04 mol) of resorcinol and 6.32 g (0.04 mol) of the ethyl monoester of itaconic acid, and also 8.8 g of Amberlyst 15 resin from Aldrich. The reaction mixture was stirred for 2 hours and then filtered off to cooling. The filtrate was concentrated and purified by flash chromatography on a silica column (eluent $CH_2Cl_2$: MeOH=50:1), to give, following recrystallization from a 3/1 hexane/ethyl acetate mixture, 4.6 g (46% yield) of the expected lactone C2 in the form of a white solid.

Melting point: 102-103° C.

The $^1$H NMR and mass spectra are in accordance with the structure of the expected product.

b) Synthesis of Compound 7

A solution of 5.5 g (22 mmol) of ethyl (7-hydroxy-2-oxo-3,4-dihydro-2H-chromen-3-yl)acetate (compound C2) in 50 ml of THF was admixed with 1.6 g (22 mmol) of butyl amine (amine A-$NH_2$ with A=$C_4H_9$) and 3 g (22 mmol) of potassium carbonate. The mixture was stirred at 40° C. for 12 hours. Following filtration and concentration of the filtrate, the crude product was purified by chromatography on a silica column to give 5 g (82% yield) of the expected compound 7.

Melting point: 122-123° C.

The $^1$H NMR and mass spectra are in accordance with the structure of the expected product.

EXAMPLES 4 TO 25

Synthesis of Compounds

The procedure of Example 3b) above was repeated, using a different amine as specified in the table below:

| Example / Compound | Structure | Reactant A-$NH_2$ | Yield | Analyses |
|---|---|---|---|---|
| 4 Compound 1 | 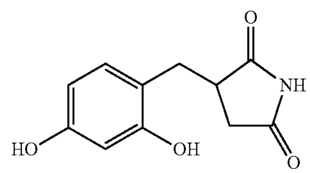 [SMILES: O=C1CC(Cc2ccc(O)cc2O)C(=O)N1] | $NH_3$ | 37 | NMR / MS in accord m.p.: 200-201° C. |
| 5 Compound 32 | 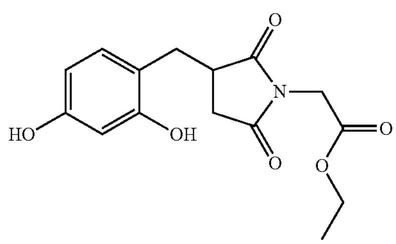 | $C_2H_5OOCCH_2NH_2$ | 84 | NMR / MS in accord m.p.: 138-139° C. |
| 6 Compound 12 | 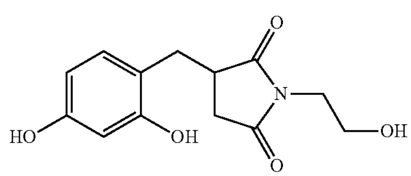 [SMILES: O=C1CC(Cc2ccc(O)cc2O)C(=O)N1CCO] | $OHC_2H_4NH_2$ | 85 | NMR / MS in accord m.p.: 126-128° C. |
| 7 Compound 55 | 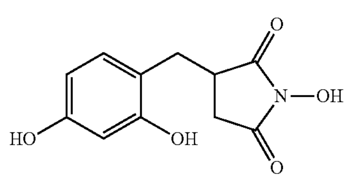 [SMILES: O=C1CC(Cc2ccc(O)cc2O)C(=O)N1O] | $NH_2OH$ | 30 | NMR / MS in accord |
| 8 Compound 60 | 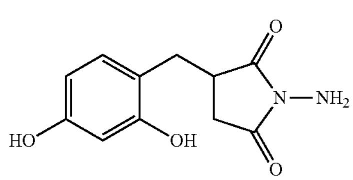 [SMILES: NN1C(=O)CC(Cc2ccc(O)cc2O)C1=O] | $H_2NNH_2$ | 19 | NMR / MS in accord m.p.: 190-192° C. |
| 9 Compound 34 | 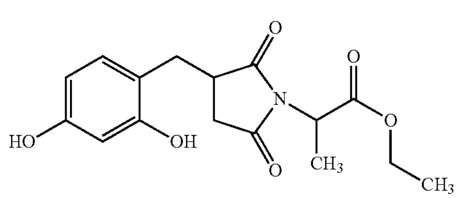 [SMILES: CCOC(=O)C(C)N1C(=O)CC(Cc2ccc(O)cc2O)C1=O] | $CH_3CH(NH_2)$—COOEt (Alanine ethyl ester) | 55 | NMR/ MS in accord |

-continued

| Example / Compound | Structure | Reactant A-NH$_2$ | Yield | Analyses |
|---|---|---|---|---|
| 10 Compound 27 | 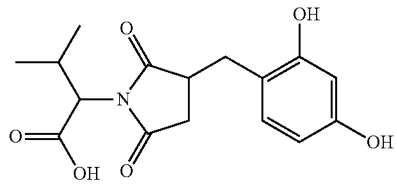 [SMILES: CC(C)C(C(=O)O)N1C(=O)CC(Cc2ccc(O)cc2O)C1=O] | (CH$_3$)$_2$CHCH—(NH$_2$)—COOH Valine | 56 | NMR/ MS in accord |
| 11 Compound 26 | 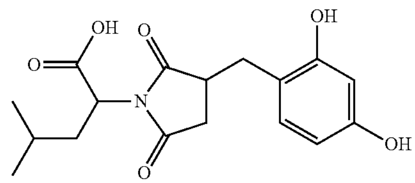 [SMILES: CC(C)CC(C(=O)O)N1C(=O)CC(Cc2ccc(O)cc2O)C1=O] | Leucine | 53 | NMR/ MS in accord |
| 12 Compound 9 | 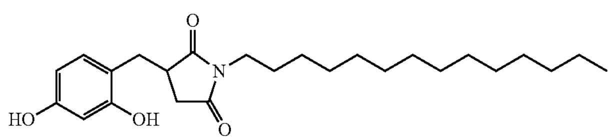 [SMILES: CCCCCCCCCCCCCCN1C(=O)CC(Cc2ccc(O)cc2O)C1=O] | C$_{14}$H$_{30}$NH$_2$ | 40 | NMR/ MS in accord |
| 13 Compound 3 | 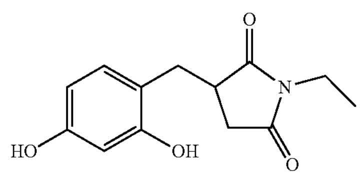 [SMILES: CCN1C(=O)CC(Cc2ccc(O)cc2O)C1=O] | Ethylamine | 33 | NMR/ MS in accord |
| 14 Compound 4 | 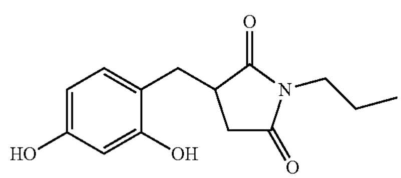 [SMILES: CCCN1C(=O)CC(Cc2ccc(O)cc2O)C1=O] | Propylamine | 15 | NMR/ MS in accord |
| 15 Compound 6 | 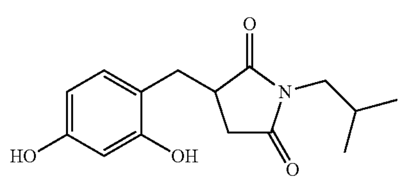 [SMILES: CC(C)CN1C(=O)CC(Cc2ccc(O)cc2O)C1=O] | Isobutylamine | 14 | NMR/ MS in accord |
| 16 Compound 15 | 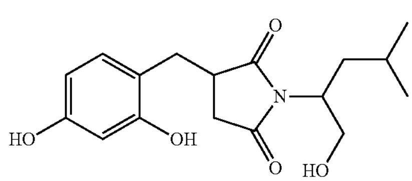 [SMILES: CC(C)CC(CO)N1C(=O)CC(Cc2ccc(O)cc2O)C1=O] | Leucinol | 30 | NMR/ MS in accord |
| 17 Compound 16 | 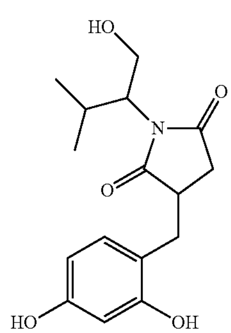 [SMILES: CC(C)C(CO)N1C(=O)CC(Cc2ccc(O)cc2O)C1=O] | Valinol | 22 | NMR/ MS in accord |

-continued

| Example / Compound | Structure | Reactant A-NH$_2$ | Yield | Analyses |
|---|---|---|---|---|
| 18 Compound 31 | 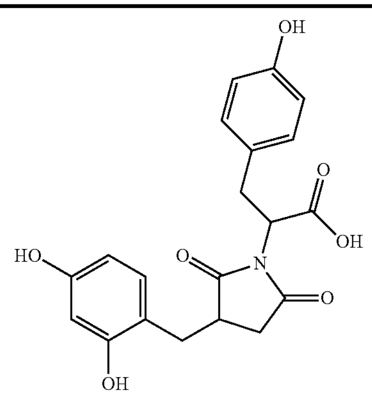 | Tyrosine | 15 | NMR/ MS in accord |
| 19 Compound 33 | 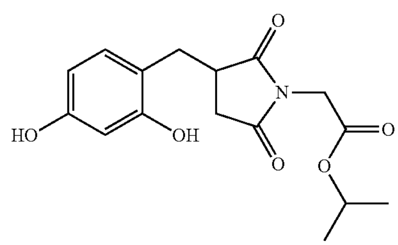 [SMILES: CC(C)OC(=O)CN1C(=O)CC(Cc2ccc(O)cc2O)C1=O] | Glycine isopropyl ester | 50 | NMR/ MS in accord |
| 20 Compound 35 | 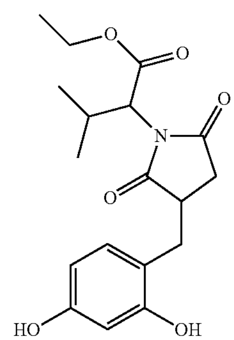 [SMILES: CCOC(=O)C(C(C)C)N1C(=O)CC(Cc2ccc(O)cc2O)C1=O] | Valine ethyl ester | 38 | NMR/ MS in accord |
| 21 Compound 37 | 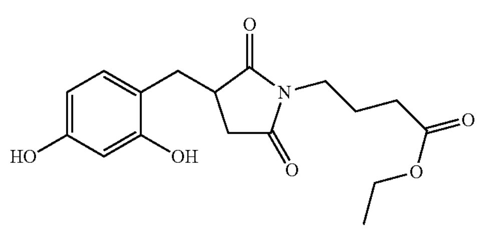 [SMILES: CCOC(=O)CCCN1C(=O)CC(Cc2ccc(O)cc2O)C1=O] | Ethyl amino- butyrate | 10 | NMR/ MS in accord |
| 22 Compound 42 | 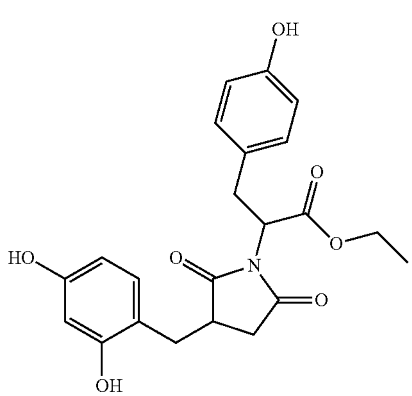 [SMILES: CCOC(=O)C(Cc1ccc(O)cc1)N1C(=O)CC(Cc2ccc(O)cc2O)C1=O] | Tyrosine ethyl ester | 42 | NMR/ MS in accord |

-continued

| Example / Compound | Structure | Reactant A-NH₂ | Yield | Analyses |
|---|---|---|---|---|
| 23 Compound 43 | 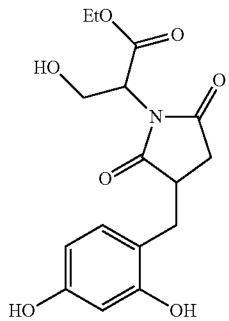 [SMILES: CCOC(=O)C(CO)N1C(=O)CC(Cc2ccc(O)cc2O)C1=O] | Serine ethyl | 25 | NMR/MS in accord |
| 24 Compound 46 | 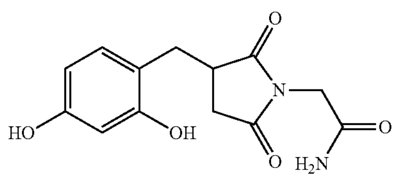 [SMILES: NC(=O)CN1C(=O)CC(Cc2ccc(O)cc2O)C1=O] | Glycine amide | 46 | NMR/MS in accord |
| 25 Compound 47 | 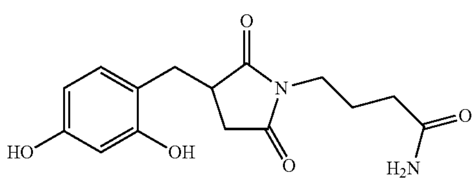 [SMILES: NC(=O)CCCN1C(=O)CC(Cc2ccc(O)cc2O)C1=O] | Amino butyric amide | 66 | NMR/MS in accord |

EXAMPLE 26

Preparation of Compound 69

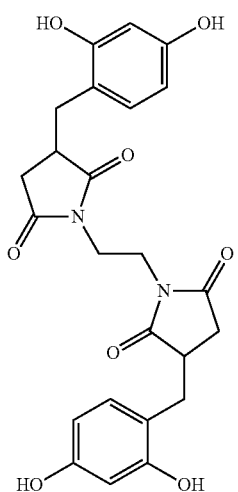 [SMILES: O=C1CC(Cc2ccc(O)cc2O)C(=O)N1CCN1C(=O)CC(Cc2ccc(O)cc2O)C1=O]

A 25 ml round-bottomed flask was charged with 1 g (0.004 mol) of ethyl (7-hydroxy-2-oxo-3,4-dihydro-2H-chromen-3-yl)acetate (compound C2), 0.829 g (0.06 mol) of potassium carbonate and 0.120 g (0.02 mol) of ethylene diamine in 10 ml of tetrahydrofuran. The reaction mixture was heated at 40° C. for 12 hours. Following filtration of the salts, the filtrate was concentrated under vacuum and then taken up in ethyl acetate. The precipitate thus obtained was filtered. It was purified on a silica column (eluent dichloromethane/methanol 95/5) to give 0.35 g (33% yield) of a white powder corresponding to the expected product.

Melting point: 125° C.

The $^1$H NMR and mass spectra are in accordance with the structure of the expected product.

EXAMPLE 27

Demonstration of the Activity on Constitutive Melanogenesis

A biological test demonstrated the depigmenting activity of compounds 1, 7, 12 and 32. The modulatory effect of compound 1 on melanogenesis was measured by the method described in patent FR-A-2 734 825 and also in the article by R. Schmidt, P. Krien and M. Régnier, Anal. Biochem., 235(2), 113-18, 1996. This test is carried out on a co-culture of keratinocytes and melanocytes.

For the compound tested, the following parameters were ascertained:

the cytotoxicity, by estimation of the incorporation of leucine, the inhibitory activity on melanin synthesis, by estimating the ratio of incorporation of thiouracil to the incorporation of leucine, relative to 100% of the control (the control corresponds to the test carried out without compound tested). The IC50 values (concentration for which 50% of the synthesis of melanin is inhibited) were ascertained.

The test was also carried out with arbutin and kojic acid, which are known depigmenting compounds.

The results are collated in the table below:
| Compound | Cytotoxicity on co-culture | IC50 |
|---|---|---|
| Arbutin | Non-cytotoxic | Not attained (or greater than 500 µM) |
| Kojic acid | 100 µM | Not attained (or greater than 500 µM) |
| Compound 7 (Example 3) 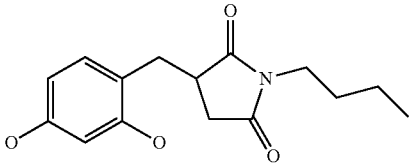 | Non-cytotoxic | 8.3 µM |
| Compound 1 (Example 4) 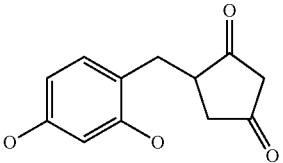 | Non-cytotoxic | 52 µM |
| Compound 32 (Example 5) 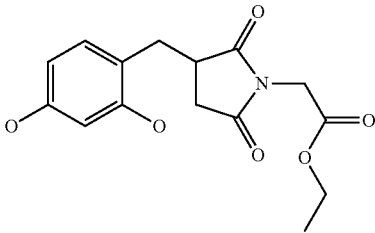 | Non-cytotoxic | 9.2 µM |
| Compound 12 (Example 6) 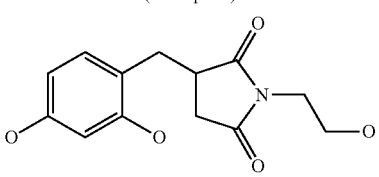 | Non-cytotoxic | 14.9 µM |

Compounds 1, 7, 12 and 32 according to the invention therefore demonstrate their efficacy in inhibiting melanogenesis and, furthermore, are more effective than arbutin and kojic acid.

EXAMPLE 28

A depigmenting gel for the skin is prepared, comprising (% by weight):

| | |
|---|---|
| Compound 7 (Example 3) | 2% |
| Carbomer (Carbopol 981 from Lubrizol) | 1% |
| Preservative | qs |
| Water | qs 100% |

When applied to the skin, the composition eliminates brown marks.

A similar composition is prepared with compound 1 (Example 15) or compound 32 (Example 5) or compound 12 (Example 6).

The invention claimed is:
1. A compound of formula (I):

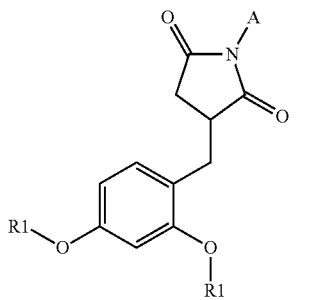

wherein:
$R_1$ is a hydrogen atom or an acetyl group; and
A is a radical selected from the group consisting of:
a) H;
b) a $C_3$-$C_8$ cyclic, a $C_3$-$C_{20}$ branched, a $C_2$-$C_{20}$ unsaturated, or a $C_1$-$C_{20}$ saturated linear alkyl group, which is optionally interrupted by one or more heteroatoms or moieties selected from the group consisting of N, O, —CO—, and a combination thereof and is optionally substituted by one or more groups independently selected from the group consisting of:
  i) —$OR_5$,
  ii) —$SR_5$,
  iii) —$NR_6R_7$,
  iv) —$CONHR_6$,
  v) —$CONR_6R_7$,
  vi) —$COOR_6$,
  vii) —$NHCONHR_6$,
  viii) a —$C(O)C_1$-$C_4$ alkyl group,
  ix) a $C_5$-$C_{12}$ (hetero)aryl group optionally comprising one or more heteroatoms selected from the group consisting of O, N and S and optionally substituted by one or more hydroxyls or one or more $C_1$-$C_8$ alkoxy radicals, and
  x) a saturated or an unsaturated, non-aromatic heterocycle comprising from 5 to 8 members and one or more heteroatoms selected from the group consisting of O, N and S and optionally substituted by one or more hydroxyls or one or more $C_1$-$C_8$ alkoxy or $C_1$-$C_4$ alkyl radicals, wherein one of the 5 to 8 members is optionally a carbonyl group;
c) a $C_5$-$C_{12}$ (hetero)aryl group optionally comprising one or more heteroatoms selected from the group consisting of O, N and S and optionally substituted by one or more hydroxyls or one or more radicals selected from the group consisting of a $C_1$-$C_8$ alkoxy group and a $C_1$-$C_8$ alkyl group;
d) —$NR_2R_3$;
e) —$OR_4$;
f) —$C(O)NHR_4$;
g) a $C(O)C_1$-$C_{10}$ alkyl group; and
h) a radical of formula (II):

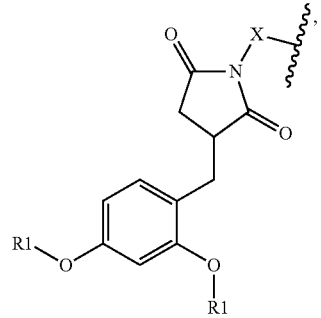

wherein:
$R_2$ and $R_3$ are each independently a radical selected from the group consisting of:
H;
a $C_3$-$C_8$ cyclic, a $C_3$-$C_{10}$ branched, a $C_2$-$C_{10}$ unsaturated, or a $C_1$-$C_{10}$ linear saturated alkyl group, which is optionally interrupted by one or more heteroatoms or moieties selected from the group consisting of N, O, —CO—, and a combination thereof and is optionally substituted by —$OR_5$; and
a $C_5$-$C_{12}$ (hetero)aryl group optionally comprising one or more heteroatoms selected from the group consisting of O, N and S and optionally substituted by one or more hydroxyls or one or more $C_1$-$C_8$ alkoxy radicals;
$R_2$ and $R_3$ optionally form, with a nitrogen, a heterocycle which comprises from 5 to 8 members, optionally comprises one or more heteroatoms or moieties selected from the group consisting of N, O and —CO—, and is optionally substituted by a $C_1$-$C_{10}$ hydrocarbon chain which optionally comprises one or more radicals selected from the group consisting of a hydroxyl group and a $C_1$-$C_4$ alkoxy group;
$R_4$ is a radical selected from the group consisting of:
H;
a $C_3$-$C_8$ cyclic, a $C_3$-$C_{10}$ branched, or a $C_1$-$C_{10}$ linear saturated alkyl group, which is optionally substituted by one or more groups independently selected from the group consisting of: —$COOR_6$, and a $C_5$-$C_{12}$ (hetero)aryl radical which optionally comprises one or more heteroatoms selected from the group consisting of O, N and S and is optionally substituted by one or more hydroxyls or one or more $C_1$-$C_8$ alkoxy radicals; and
a $C_5$-$C_{12}$ (hetero)aryl group which optionally comprises one or more heteroatoms selected from the group consisting of O, N and S and is optionally substituted by one or more hydroxyls or one or more $C_1$-$C_8$ alkoxy radicals;

$R_5$ is selected from the group consisting of H and a $C_3$-$C_8$ cyclic, a $C_2$-$C_{10}$ unsaturated, a $C_3$-$C_{10}$ branched, or a $C_1$-$C_{10}$ linear saturated alkyl hydrocarbon group;

$R_6$ and $R_7$ are each independently selected from the group consisting of:

H;

a $C_3$-$C_8$ cyclic, a $C_2$-$C_{10}$ unsaturated, a $C_3$-$C_{10}$ branched, or a $C_1$-$C_{10}$ linear saturated alkyl hydrocarbon group; and a ($C_1$-$C_4$)alkyl-$C_6$ (hetero)aryl group optionally comprising a nitrogen atom;

$R_6$ and $R_7$ optionally form, with a nitrogen, a heterocycle which comprises from 5 to 8 members, optionally comprises one or more heteroatoms or moieties selected from the group consisting of N, O and —CO—, and is optionally substituted by a $C_1$-$C_{10}$ hydrocarbon chain; and X is a $C_3$-$C_8$ cyclic, a $C_3$-$C_{10}$ branched, or a $C_1$-$C_{10}$ linear saturated hydrocarbon chain;

a $C_6$-$C_{12}$ arylene group;

a $C_1$-$C_4$ alkylene-$C_6$-$C_8$ cycloalkylene-$C_1$-$C_4$ alkylene group; or a $C_1$-$C_4$ alkylene-phenylene-$C_1$-$C_4$ alkylene group, which is optionally substituted by one or more radicals independently selected from the group consisting of —OH and —COOR$_8$, wherein $R_8$ is H, a $C_3$-$C_8$ cyclic, a $C_2$-$C_{10}$ unsaturated, a $C_3$-$C_{10}$ branched, or a $C_1$-$C_{20}$ linear saturated alkyl hydrocarbon group.

2. The compound according to claim 1, wherein:

A is a radical selected from the group consisting of:

H;

a $C_3$-$C_8$ cyclic, a $C_3$-$C_{16}$ branched, a $C_2$-$C_{16}$ unsaturated, or a $C_1$-$C_{16}$ linear saturated alkyl group, which is optionally interrupted by one or more heteroatoms or moieties selected from the group consisting of N, O, —CO— and —NHC(O)— and is optionally substituted by one or more groups independently selected from the group consisting of:

—OH, a $C_1$-$C_4$ alkoxy group,

—COOR$_6$,

—CONR$_6$R$_7$, a phenyl group which is optionally substituted by one or more hydroxyls or one or more $C_1$-$C_4$ alkoxy radicals, and a saturated or an unsaturated heterocycle comprising from 5 to 8 members and one or more heteroatoms selected from the group consisting of O, N and S, wherein one of the 5 to 8 members is optionally a carbonyl group;

a $C_5$-$C_{12}$ aryl group, which is optionally substituted by one or more radicals independently selected from the group consisting of OH, a $C_1$-$C_4$ alkoxy group, and a $C_1$-$C_4$ alkyl group;

—NR$_2$R$_3$;

—OR$_4$;

—C(O)NHR$_4$;

and a radical of formula (II), wherein $R_2$ and $R_3$ each are independently selected from the group consisting of:

H, a $C_3$-$C_8$ cyclic, a $C_2$-$C_8$ unsaturated, a $C_3$-$C_8$ branched, or a $C_1$-$C_8$ linear saturated alkyl group, which is optionally interrupted by an oxygen atom and optionally substituted by a hydroxyl group or a $C_1$-$C_4$ alkoxy group, and a $C_5$-$C_{12}$ aryl group which is optionally substituted by one or more hydroxyls and one or more $C_1$-$C_4$ alkoxy radicals;

$R_2$ and $R_3$ optionally form, with a nitrogen, a heterocycle comprising from 5 to 8 members, wherein the heterocycle optionally comprises one or more oxygen atoms or is optionally substituted by a $C_1$-$C_6$ hydrocarbon chain optionally comprising one or more hydroxyls or $C_1$-$C_4$ alkoxys;

$R_4$ is a radical selected from the group consisting of H and a $C_3$-$C_8$ branched or a $C_1$-$C_8$ linear saturated alkyl group which is optionally substituted by one or more groups independently selected from the group consisting of —COOR$_6$ and a $C_5$-$C_{12}$ aryl radical;

$R_6$ and $R_7$ are each independently H or a $C_3$-$C_8$ cyclic, a $C_2$-$C_{12}$ unsaturated, a $C_3$-$C_8$ branched, or a $C_1$-$C_8$ linear saturated alkyl group; and X is a $C_3$-$C_8$ cyclic, a $C_3$-$C_6$ branched or a $C_1$-$C_6$ linear saturated hydrocarbon chain, or a $C_6$-$C_{12}$ arylene group, which is optionally substituted by one or more radicals independently selected from the group consisting of OH and a $C_1$-$C_6$ alkyl group.

3. The compound according to claim 1, wherein:

A is a radical selected from the group consisting of:

H;

a $C_3$-$C_8$ cyclic, a $C_3$-$C_{16}$ branched, a $C_2$-$C_{16}$ unsaturated, or a $C_1$-$C_{16}$ linear saturated alkyl group, which is optionally interrupted by one or more heteroatoms selected from the group consisting of N and O and is optionally substituted by one or more groups independently selected from the group consisting of:

—OH, a $C_1$-$C_4$ alkoxy group,

—CONH$_2$,

—COOR$_6$, a phenyl group which is optionally substituted by one or more hydroxyls or one or more $C_1$-$C_4$ alkoxy radicals, and a saturated or an unsaturated, non-aromatic heterocycle comprising from 5 to 8 members and one or more nitrogen atoms, wherein one of the 5 to 8 members is optionally a carbonyl moiety;

a $C_5$-$C_{12}$ aryl group;

—NR$_2$R$_3$;

—OR$_4$;

and a radical of formula (II), wherein $R_2$ and $R_3$ are each independently H; a $C_3$-$C_8$ cyclic, a $C_2$-$C_6$ unsaturated, a $C_3$-$C_6$ branched, or a $C_1$-$C_6$ linear saturated alkyl group; or a $C_5$-$C_{12}$ aryl group, $R_2$ and $R_3$ optionally form, with a nitrogen, a heterocycle comprising from 5 to 8 members, wherein the heterocycle optionally comprises an oxygen atom and is optionally substituted by a $C_1$-$C_6$ hydrocarbon chain which optionally comprises one or more radicals selected from the group consisting of a hydroxyl and a $C_1$-$C_4$ alkoxy group, $R_4$ is H or a $C_3$-$C_6$ branched or a $C_1$-$C_6$ linear saturated alkyl group which is optionally substituted by one or more groups independently selected from the group consisting of —COOH and a $C_5$-$C_{12}$ aryl radical, $R_6$ is H, a $C_3$-$C_4$ cyclic, a $C_2$-$C_4$ unsaturated, a $C_3$-$C_4$ branched, or a $C_1$-$C_4$ linear saturated alkyl group, and X is a $C_3$-$C_8$ cyclic, a $C_3$-$C_6$ branched, or a $C_1$-$C_6$ linear saturated hydrocarbon chain, or a $C_6$-$C_{12}$ arylene group, which is optionally substituted by one or more hydroxyl radicals.

4. The compound according to claim 1, wherein $R_1$ is H.

5. The compound according to claim 4, wherein A is a radical selected from the group consisting of:

H;

a $C_3$-$C_{16}$ branched or a $C_1$-$C_{16}$ saturated linear alkyl group;

a $C_3$-$C_8$ branched or a $C_1$-$C_8$ saturated linear alkyl group which is substituted by one or two hydroxyl groups and is optionally substituted by —$SR_5$;

a phenyl or a benzyl group;

a $C_3$-$C_8$ branched or a $C_1$-$C_8$ alkyl group which is substituted by a phenyl group which is optionally substituted by one or more hydroxyl groups or a $C_1$-$C_4$ alkoxy group;

a $C_3$-$C_8$ branched or a $C_1$-$C_8$ saturated linear alkyl group which is substituted by a —COOH group, which is optionally substituted by $SR_5$;

a $C_3$-$C_8$ branched or a $C_1$-$C_8$ saturated linear alkyl group which is substituted by a —$COOR_6$ group, and is optionally substituted by a hydroxyl group or —$SR_5'$;

a $C_3$-$C_8$ branched or a $C_1$-$C_8$ saturated linear alkyl group which is substituted by a —$CONH_2$ group, which is optionally substituted by a hydroxyl or a phenyl group which is optionally substituted by one or more hydroxyls, or —$COOR_6$;

a $C_3$-$C_6$ branched or a $C_2$-$C_6$ linear alkyl group interrupted by a —CONH— group and substituted by a COOH group;

a $C_5$-$C_6$ cyclic alkyl group interrupted by a —CONH— group;

a $C_5$-$C_6$ cyclic alkyl group interrupted by an oxygen atom; and a radical of formula (II), wherein:

$R_2$ and $R_3$ are each independently H, a $C_3$-$C_6$ branched or $C_1$-$C_6$ linear saturated alkyl group, or a phenyl group, $R_2$ and $R_3$ optionally form, with a nitrogen, a heterocycle which comprises from 5 or 6 members and optionally comprises an oxygen atom, wherein the heterocycle is optionally substituted by a $C_1$-$C_6$ hydrocarbon chain optionally comprising one or more radicals selected from the group consisting of a hydroxyl group and a $C_1$-$C_4$ alkoxy group, $R_4$ is H, or a $C_3$-$C_6$ branched or a $C_1$-$C_6$ linear saturated alkyl group which is optionally substituted by —COOH or a phenyl group, $R_5$ is H or $C_1$-$C_4$ alkyl, $R_5'$ is H, a $C_1$-$C_4$ alkyl group, or a phenyl group which is optionally substituted by one or more hydroxyls or an imidazole radical, $R_6$ is a $C_1$-$C_6$ alkyl group, and X is a $C_5$-$C_8$ cyclic, a $C_3$-$C_6$ branched, or a $C_1$-$C_6$ linear saturated hydrocarbon chain, or a phenylene group, which is optionally substituted by one or more hydroxyl groups.

6. The compound according to claim 1, wherein the compound is selected from the group consisting of:

3-(2,4-dihydroxybenzyl)pyrrolidine-2,5-dione,
3-(2,4-dihydroxybenzyl)-1-methylpyrrolidine-2,5-dione,
3-(2,4-dihydroxybenzyl)-1-ethylpyrrolidine-2,5-dione,
3-(2,4-dihydroxybenzyl)-1-propylpyrrolidine-2,5-dione,
3-(2,4-dihydroxybenzyl)-1-isopropylpyrrolidine-2,5-dione,
3-(2,4-dihydroxybenzyl)-1-isobutylpyrrolidine-2,5-dione,
3-(2,4-dihydroxybenzyl)-1-butylpyrrolidine-2,5-dione,
4-[(1-butyl-2,5-dioxopyrrolidin-3-yl)methyl]benzene-1,3-diyl diacetate,
3-(2,4-dihydroxybenzyl)-1-tetradecylpyrrolidine-2,5-dione,
3-(2,4-dihydroxybenzyl)-1-phenylpyrrolidine-2,5-dione,
3-(2,4-dihydroxybenzyl)-1-benzylpyrrolidine-2,5-dione,
3-(2,4-dihydroxybenzyl)-1-(2-hydroxyethyl)pyrrolidine-2,5-dione,
3-(2,4-dihydroxybenzyl)-1-(1-hydroxypropan-2-yl)pyrrolidine-2,5-dione,
3-(2,4-dihydroxybenzyl)-1-(1-hydroxy-3-methylpentan-2-yl)pyrrolidine-2,5-dione,
3-(2,4-dihydroxybenzyl)-1-(1-hydroxy-4-methylpentan-2-yl)pyrrolidine-2,5-dione,
3-(2,4-dihydroxybenzyl)-1-(1-hydroxy-3-methylbutan-2-yl)pyrrolidine-2,5-dione,
3-(2,4-dihydroxybenzyl)-1-(2,3-dihydroxypropyl)pyrrolidine-2,5-dione,
3-(2,4-dihydroxybenzyl)-1-(1,3-dihydroxypropan-2-yl)pyrrolidine-2,5-dione,
3-(2,4-dihydroxybenzyl)-1-[1-hydroxy-4-(methylsulphanyl)butan-2-yl]pyrrolidine-2,5-dione,
3-(2,4-dihydroxybenzyl)-1-(1-hydroxy-3-phenylpropan-2-yl)pyrrolidine-2,5-dione,
3-(2,4-dihydroxybenzyl)-1-[2-(4-hydroxyphenyl)ethyl]pyrrolidine-2,5-dione,
3-(2,4-dihydroxybenzyl)-1-[2-(4-hydroxy-3-methoxyphenyl)ethyl]pyrrolidine-2,5-dione,
[3-(2,4-dihydroxybenzyl)-2,5-dioxopyrrolidin-1-yl]acetic acid,
2-[3-(2,4-dihydroxybenzyl)-2,5-dioxopyrrolidin-1-yl]propanoic acid,
2-[3-(2,4-dihydroxybenzyl)-2,5-dioxopyrrolidin-1-yl]-3-methylpentanoic acid,
2-[3-(2,4-dihydroxybenzyl)-2,5-dioxopyrrolidin-1-yl]-4-methylpentanoic acid,
2-[3-(2,4-dihydroxybenzyl)-2,5-dioxopyrrolidin-1-yl]-3-methylbutanoic acid,
4-[3-(2,4-dihydroxybenzyl)-2,5-dioxopyrrolidin-1-yl]butanoic acid,
2-[3-(2,4-dihydroxybenzyl)-2,5-dioxopyrrolidin-1-yl]-3-sulphanylpropanoic acid,
2-[3-(2,4-dihydroxybenzyl)-2,5-dioxopyrrolidin-1-yl]-4-(methylsulphanyl)butanoic acid,
2-[3-(2,4-dihydroxybenzyl)-2,5-dioxopyrrolidin-1-yl]-3-(4-hydroxyphenyl)propanoic acid,
ethyl[3-(2,4-dihydroxybenzyl)-2,5-dioxopyrrolidin-1-yl]acetate,
isopropyl[3-(2,4-dihydroxybenzyl)-2,5-dioxopyrrolidin-1-yl]acetate,
ethyl 2-[3-(2,4-dihydroxybenzyl)-2,5-dioxopyrrolidin-1-yl]propanoate,
ethyl 2-[3-(2,4-dihydroxybenzyl)-2,5-dioxopyrrolidin-1-yl]-3-methylbutanoate,
ethyl 2-[3-(2,4-dihydroxybenzyl)-2,5-dioxopyrrolidin-1-yl]-3-(1H-imidazol-4-yl)propanoate,
ethyl 4-[3-(2,4-dihydroxybenzyl)-2,5-dioxopyrrolidin-1-yl]butanoate,
isopropyl 4-[3-(2,4-dihydroxybenzyl)-2,5-dioxopyrrolidin-1-yl]butanoate, ethyl 2-[3-(2,4-dihydroxybenzyl)-2,5-dioxopyrrolidin-1-yl]-3-methylpentanoate,
ethyl 2-[3-(2,4-dihydroxybenzyl)-2,5-dioxopyrrolidin-1-yl]-4-methylpentanoate,
ethyl 2-[3-(2,4-dihydroxybenzyl)-2,5-dioxopyrrolidin-1-yl]-3-phenylpropanoate,
ethyl 2-[3-(2,4-dihydroxybenzyl)-2,5-dioxopyrrolidin-1-yl]-3-(4-hydroxyphenyl)propanoate,
ethyl 2-[3-(2,4-dihydroxybenzyl)-2,5-dioxopyrrolidin-1-yl]-3-hydroxypropanoate,
ethyl 2-[3-(2,4-dihydroxybenzyl)-2,5-dioxopyrrolidin-1-yl]-3-sulphanylpropanoate,
ethyl 2-[3-(2,4-dihydroxybenzyl)-2,5-dioxopyrrolidin-1-yl]-4-(methylsulphanyl)butanoate,
2-[3-(2,4-dihydroxybenzyl)-2,5-dioxopyrrolidin-1-yl]acetamide,
4-[3-(2,4-dihydroxybenzyl)-2,5-dioxopyrrolidin-1-yl]butanamide,
2-[3-(2,4-dihydroxybenzyl)-2,5-dioxopyrrolidin-1-yl]-3-phenylpropanamide,
2-[3-(2,4-dihydroxybenzyl)-2,5-dioxopyrrolidin-1-yl]-3-(4-hydroxyphenyl)propanamide,
2-[3-(2,4-dihydroxybenzyl)-2,5-dioxopyrrolidin-1-yl]-3-hydroxypropanamide,
ethyl 4-amino-2-[3-(2,4-dihydroxybenzyl)-2,5-dioxopyrrolidin-1-yl]-4-oxobutanoate,
N-{2-[3-(2,4-dihydroxybenzyl)-2,5-dioxopyrrolidin-1-yl]propanoyl}alanine,
3-(2,4-dihydroxybenzyl)-1-(2-oxoazepan-3-yl)pyrrolidine-2,5-dione,
3-(2,4-dihydroxybenzyl)-1-(tetrahydrofuran-2-ylmethyl)pyrrolidine-2,5-dione,
3-(2,4-dihydroxybenzyl)-1-hydroxypyrrolidine-2,5-dione,
3-(2,4-dihydroxybenzyl)-1-methoxypyrrolidine-2,5-dione,
3-(2,4-dihydroxybenzyl)-1-ethoxypyrrolidine-2,5-dione,
{[3-(2,4-dihydroxybenzyl)-2,5-dioxopyrrolidin-1-yl]oxy}acetic acid,
3-(2,4-dihydroxybenzyl)-1-benzyloxypyrrolidine-2,5-dione,
1-amino-3-(2,4-dihydroxybenzyl)pyrrolidine-2,5-dione,
3-(2,4-dihydroxybenzyl)-1-(dimethylamino)pyrrolidine-2,5-dione,
3-(2,4-dihydroxybenzyl)-1-(morpholin-4-yl)pyrrolidine-2,5-dione,
3-(2,4-dihydroxybenzyl)-2'-(methoxymethyl)-1,1'-bipyrrolidine-2,5-dione,
3-(2,4-dihydroxybenzyl)-1-(phenylamino)pyrrolidine-2,5-dione,
1,1'-cyclohexane-1,3-diylbis[3-(2,4-dihydroxybenzyl)pyrrolidine-2,5-dione],
1,1'-(cyclohexane-1,3-diyldimethanediyl)bis[3-(2,4-dihydroxybenzyl)pyrrolidine-2,5-dione],
1,1'-propane-1,3-diylbis[3-(2,4-dihydroxybenzyl)pyrrolidine-2,5-dione],
1,1'-(2-hydroxypropane-1,3-diyl)bis[3-(2,4-dihydroxybenzyl)pyrrolidine-2,5-dione],
1,1'-ethane-1,2-diylbis[3-(2,4-dihydroxybenzyl)pyrrolidine-2,5-dione],
1,1'-benzene-1,4-diylbis[3-(2,4-dihydroxybenzyl)pyrrolidine-2,5-dione],
1,1'-cyclohexane-1,4-diylbis[3-(2,4-dihydroxybenzyl)pyrrolidine-2,5-dione],
1,1'-cyclohexane-1,2-diylbis[3-(2,4-dihydroxybenzyl)pyrrolidine-2,5-dione],
ethyl 2,6-bis[3-(2,4-dihydroxybenzyl)-2,5-dioxopyrrolidin-1-yl]hexanoate,
3-(2,4-dihydroxybenzyl)-1-(2-hydroxyethyl)pyrrolidine-2,5-dione,
3-(2,4-dihydroxybenzyl)-1-(1-hydroxypropan-2-yl)pyrrolidine-2,5-dione,
3-(2,4-dihydroxybenzyl)-1-(1-hydroxy-3-methylpentan-2-yl)pyrrolidine-2,5-dione,
3-(2,4-dihydroxybenzyl)-1-(1-hydroxy-4-methylpentan-2-yl)pyrrolidine-2,5-dione,
3-(2,4-dihydroxybenzyl)-1-(1-hydroxy-3-methylbutan-2-yl)pyrrolidine-2,5-dione,
3-(2,4-dihydroxybenzyl)-1-(2,3-dihydroxypropyl)pyrrolidine-2,5-dione, and
3-(2,4-dihydroxybenzyl)-1-(1,3-dihydroxypropan-2-yl)pyrrolidine-2,5-dione.

7. A composition, comprising, in a physiologically acceptable medium, the compound according to claim 1.

8. The composition according to claim 7, wherein the compound is present in an amount of from 0.01% to 10% by weight, relative to a total weight of the composition.

9. The composition according to claim 7, further comprising an adjuvant selected from the group consisting of water, an organic solvent, a hydrocarbon oil, a silicone oil, a wax, a pigment, a filler, a dye, a surfactant, an emulsifier, an active cosmetic ingredient, a UV filter, a polymer, a thickener, a preservative, a fragrance, a bactericide, a ceramide, an odour absorber, and an antioxidant.

10. The composition according to claim 7, further comprising an active ingredient selected from the group consisting of
a desquamating agent;
a calmative;
an organic or inorganic light stabilizer;
a moisturizer;
a depigmenting or propigmenting agent;
an anti-glycation agent;
a NO-synthase inhibitor;
an agent stimulating a synthesis of dermal or epidermal macromolecules or preventing a degradation of the macromolecules;
an agent stimulating fibroblast, keratinocyte proliferation, or both;
an agent stimulating keratinocyte differentiation;
a muscle relaxant;
a dermal decontractant;
a tensioning agent;
an anti-pollution agent;
a free-radical scavenger;
an agent acting on microcirculation;
an agent acting on energy metabolism of cells; and
a mixture thereof.

11. A non-therapeutic, cosmetic method for depigmenting, lightening, or whitening a keratin material, the method comprising:
applying the composition according to claim 7 to the keratin material in need thereof.

12. The method according to claim 11, wherein the keratin material is skin.

13. A whitening, lightening or depigmenting agent for a keratin material, comprising the compound according to claim 1.

14. A process for preparing the compound according to claim 1, the process comprising:
reacting resorcinol with itaconic acid, anhydride of itaconic acid, or an ester of itaconic acid of formula (B1)

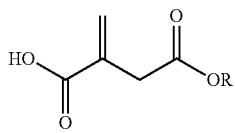

wherein R is H, a $C_3$-$C_6$ branched alkyl group, or a $C_1$-$C_6$ linear alkyl group, thereby obtaining a compound of formula (III)

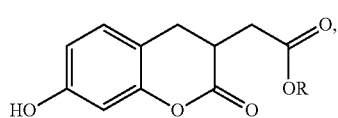

subsequently reacting the compound of formula (III), optionally in an activated form, with a A-$NH_2$ compound, optionally in the presence of a basic or an acidic catalyst and optionally at a temperature of from 15° C. to 200° C., and optionally carrying out an acetylation reaction, thereby obtaining the compound of formula (I).

15. A compound of formula (III)

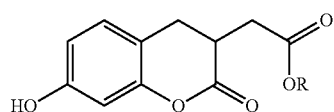

wherein R is H, a $C_3$-$C_6$ branched alkyl group, or a $C_1$-$C_6$ linear alkyl group.

16. The compound according to claim 1, wherein A is a radical of formula (II) and all $R_1$ in formula (I) are identical radicals.

17. The compound according to claim 1, wherein the compound is a salt, an optical isomer or a racemate thereof.

* * * * *